(12) United States Patent
Hartwell

(10) Patent No.: US 11,364,151 B2
(45) Date of Patent: Jun. 21, 2022

(54) WOUND DRESSING

(71) Applicant: Smith & Nephew PLC, Watford (GB)

(72) Inventor: Edward Yerbury Hartwell, York (GB)

(73) Assignee: Smith & Nephew PLC, Watford (GB)

( * ) Notice: Subject to any disclaimer, the term of this patent is extended or adjusted under 35 U.S.C. 154(b) by 511 days.

(21) Appl. No.: 15/460,123

(22) Filed: Mar. 15, 2017

(65) Prior Publication Data

US 2017/0181897 A1 Jun. 29, 2017

Related U.S. Application Data

(63) Continuation of application No. 14/869,826, filed on Sep. 29, 2015, now Pat. No. 10,016,309, which is a
(Continued)

(30) Foreign Application Priority Data

Nov. 21, 2007 (GB) ..................................... 0722820
Sep. 17, 2008 (GB) ..................................... 0817020

(51) Int. Cl.
*A61M 1/00* (2006.01)
*A61F 13/00* (2006.01)
(Continued)

(52) U.S. Cl.
CPC ...... *A61F 13/022* (2013.01); *A61F 13/00063* (2013.01); *A61F 13/00068* (2013.01); *A61F 13/025* (2013.01); *A61F 13/0206* (2013.01); *A61F 13/0209* (2013.01); *A61F 13/0216* (2013.01); *A61F 13/0226* (2013.01);
(Continued)

(58) Field of Classification Search
CPC ...... A61M 1/0088–0092; A61M 27/00; A61M 1/90; A61M 1/92; A61F 13/00029; A61F 13/00046; A61F 13/00068; A61F 13/02–0293; A61F 2013/00089–00982
See application file for complete search history.

(56) References Cited

U.S. PATENT DOCUMENTS

| | | |
|---|---|---|
| 695,270 A | 3/1902 | Beringer |
| 1,480,562 A | 1/1924 | Mock |
| (Continued) | | |

FOREIGN PATENT DOCUMENTS

| | | |
|---|---|---|
| CN | 2186074 | 12/1994 |
| CN | 201664463 | 12/2010 |
| (Continued) | | |

OTHER PUBLICATIONS

US 6,216,701 B1, 04/2001, Heaton et al. (withdrawn)
(Continued)

*Primary Examiner* — Benjamin J Klein
(74) *Attorney, Agent, or Firm* — Knobbe, Martens, Olson & Bear, LLP

(57) ABSTRACT

A method and apparatus are disclosed for dressing a wound. The apparatus comprises an absorbent layer for absorbing wound exudate, a liquid impermeable, gas permeable filter layer over the absorbent layer, a cover layer comprising at least one orifice and a first liquid and gas permeable transmission layer underlying the absorbent layer. The transmission layer is in fluid communication with the filter layer.

16 Claims, 3 Drawing Sheets

Figure 1:
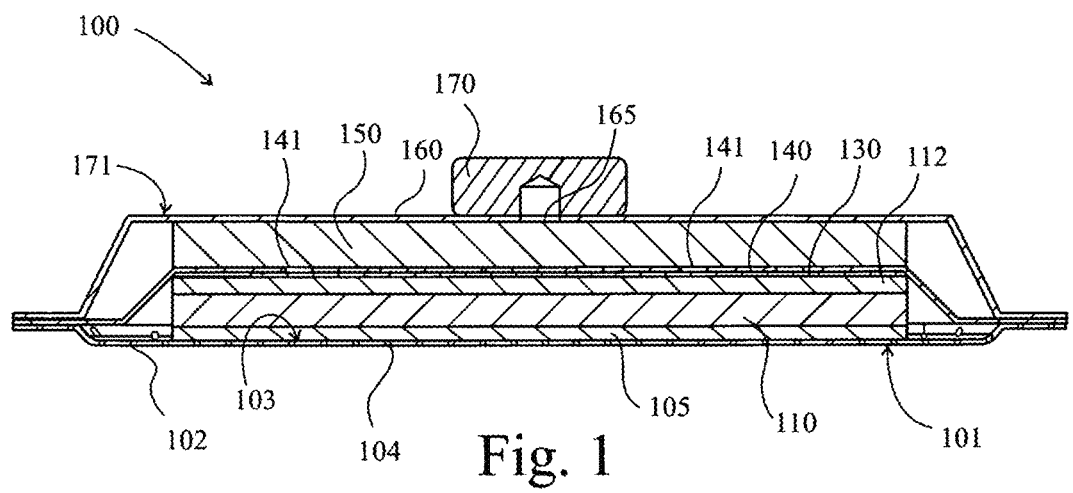

Related U.S. Application Data continuation of application No. 14/259,026, filed on Apr. 22, 2014, now Pat. No. 9,956,121, which is a continuation of application No. 12/744,277, filed as application No. PCT/GB2008/051090 on Nov. 20, 2008, now Pat. No. 8,764,732.

(51) Int. Cl.
   *A61M 27/00* (2006.01)
   *A61F 13/02* (2006.01)

(52) U.S. Cl.
   CPC ........... *A61F 13/0253* (2013.01); *A61M 1/90* (2021.05); *A61M 1/962* (2021.05); *A61M 27/00* (2013.01); *A61F 2013/0028* (2013.01); *A61F 2013/00246* (2013.01); *A61F 2013/00536* (2013.01); *A61M 2205/7536* (2013.01)

(56) References Cited

U.S. PATENT DOCUMENTS

| | | |
|---|---|---|
| 2,280,915 A | 4/1942 | Johnson |
| 2,367,690 A | 7/1943 | Purdy |
| 2,568,933 A | 9/1951 | Robbins |
| 2,632,443 A | 3/1953 | Lesher |
| 2,682,873 A | 7/1954 | Evans et al. |
| 2,910,763 A | 8/1955 | Lauterbach |
| 3,115,138 A | 12/1963 | McElvenny et al. |
| 3,367,332 A | 2/1968 | Groves |
| 3,572,340 A | 3/1971 | Lloyd et al. |
| 3,874,387 A | 4/1975 | Barbieri |
| 3,972,328 A | 8/1976 | Chen |
| 3,993,080 A | 11/1976 | Loseff |
| 4,029,598 A | 6/1977 | Neisius et al. |
| RE29,319 E | 7/1977 | Nordby et al. |
| 4,102,342 A | 7/1978 | Akiyama et al. |
| 4,112,947 A | 9/1978 | Nehring |
| 4,117,551 A | 9/1978 | Books et al. |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,941 A | 9/1980 | Stivala |
| 4,224,945 A | 9/1980 | Cohen |
| 4,316,466 A | 2/1982 | Babb |
| 4,382,441 A | 5/1983 | Svedman |
| 4,398,910 A | 8/1983 | Blake et al. |
| 4,465,485 A | 8/1984 | Kashmer et al. |
| 4,466,431 A | 8/1984 | Tharrat et al. |
| 4,529,402 A | 7/1985 | Weilbacher et al. |
| 4,534,356 A | 8/1985 | Papadakis |
| 4,538,920 A | 9/1985 | Drake et al. |
| 4,569,674 A | 2/1986 | Phillips |
| 4,573,965 A | 3/1986 | Russo |
| 4,608,041 A | 8/1986 | Nielsen |
| 4,624,656 A | 11/1986 | Clark et al. |
| 4,655,754 A | 4/1987 | Richmond et al. |
| 4,655,766 A | 4/1987 | Theeuwes et al. |
| 4,681,562 A | 7/1987 | Beck et al. |
| 4,710,165 A | 12/1987 | McNeil et al. |
| 4,728,499 A | 3/1988 | Fehder |
| 4,753,536 A | 6/1988 | Spehar et al. |
| 4,767,026 A | 8/1988 | Keller |
| 4,767,943 A | 8/1988 | Adler et al. |
| 4,771,919 A | 9/1988 | Ernst |
| 4,778,446 A | 10/1988 | Jensen |
| 4,792,328 A | 12/1988 | Beck et al. |
| 4,813,942 A | 3/1989 | Alvarez |
| 4,826,494 A | 5/1989 | Richmond et al. |
| 4,828,546 A | 5/1989 | McNeil et al. |
| 4,872,450 A | 10/1989 | Austad |
| 4,921,488 A | 5/1990 | Maitz et al. |
| 4,936,834 A | 6/1990 | Beck et al. |
| 4,969,880 A | 11/1990 | Zamierowski |
| 4,972,829 A | 11/1990 | Knerr |
| 4,979,944 A | 12/1990 | Luzsicza |
| 4,994,022 A | 2/1991 | Steffi et al. |
| 5,010,115 A | 4/1991 | Grisoni |
| 5,055,195 A | 10/1991 | Trasch et al. |
| 5,055,198 A | 10/1991 | Shettigar |
| 5,056,510 A | 10/1991 | Gilman |
| 5,060,642 A | 10/1991 | Gilman |
| 5,061,258 A | 10/1991 | Martz |
| 5,064,653 A | 11/1991 | Sessions et al. |
| 5,073,172 A | 12/1991 | Fell |
| 5,080,493 A | 1/1992 | McKown et al. |
| 5,100,396 A | 3/1992 | Zamierowski |
| 5,134,994 A | 8/1992 | Say |
| 5,152,757 A | 10/1992 | Eriksson |
| 5,167,613 A | 12/1992 | Karami et al. |
| 5,176,663 A | 1/1993 | Svedman et al. |
| 5,181,905 A | 1/1993 | Flam |
| 5,215,519 A | 6/1993 | Shettigar |
| 5,222,714 A | 6/1993 | Morinigo et al. |
| 5,234,419 A | 8/1993 | Bryant et al. |
| 5,238,732 A | 8/1993 | Krishnan |
| 5,249,709 A | 10/1993 | Duckworth et al. |
| 5,261,893 A | 11/1993 | Zamierowski |
| 5,266,326 A | 11/1993 | Barry et al. |
| 5,266,928 A | 11/1993 | Johnson |
| 5,279,608 A | 1/1994 | Cherif Cheikh |
| 5,291,822 A | 3/1994 | Alsobrooks et al. |
| 5,328,614 A | 7/1994 | Matsumura |
| 5,333,760 A | 8/1994 | Simmen et al. |
| 5,349,896 A | 9/1994 | Connelly et al. |
| 5,358,494 A | 10/1994 | Svedman |
| 5,380,280 A | 1/1995 | Peterson |
| D357,743 S | 4/1995 | Bilitz et al. |
| 5,417,743 A | 5/1995 | Dauber |
| 5,437,651 A | 8/1995 | Todd et al. |
| 5,445,604 A | 8/1995 | Lang |
| 5,449,003 A | 9/1995 | Sugimura |
| 5,449,347 A | 9/1995 | Preen et al. |
| 5,456,745 A | 10/1995 | Rorefer et al. |
| 5,466,229 A | 11/1995 | Elson |
| 5,489,280 A | 2/1996 | Russell |
| 5,498,338 A | 3/1996 | Kruger et al. |
| 5,527,293 A | 6/1996 | Zamierowski |
| 5,536,233 A | 7/1996 | Khouri |
| 5,549,584 A * | 8/1996 | Gross .................. A61M 1/0088 604/313 |
| 5,582,596 A | 12/1996 | Fukunaga et al. |
| 5,583,114 A | 12/1996 | Barrows et al. |
| 5,609,271 A | 3/1997 | Keller et al. |
| 5,612,050 A | 3/1997 | Rowe et al. |
| 5,624,423 A | 4/1997 | Anjur et al. |
| 5,632,731 A | 5/1997 | Patel |
| 5,634,391 A | 6/1997 | Eady |
| 5,636,643 A | 6/1997 | Argenta et al. |
| 5,643,189 A | 7/1997 | Masini |
| 5,645,081 A | 7/1997 | Argenta et al. |
| 5,660,823 A | 8/1997 | Chakrabarti et al. |
| 5,662,583 A | 9/1997 | Khouri |
| 5,676,525 A | 10/1997 | Berner et al. |
| 5,676,634 A | 10/1997 | Khouri |
| 5,678,564 A | 10/1997 | Lawrence et al. |
| 5,687,633 A | 11/1997 | Eady |
| 5,693,013 A | 12/1997 | Geuder |
| 5,695,445 A | 12/1997 | Khouri |
| 5,700,477 A | 12/1997 | Rosenthal et al. |
| 5,701,917 A | 12/1997 | Khouri |
| 5,707,499 A | 1/1998 | Joshi et al. |
| 5,717,030 A | 2/1998 | Dunn et al. |
| 5,730,587 A | 3/1998 | Snyder et al. |
| 5,733,337 A | 3/1998 | Carr et al. |
| 5,743,170 A | 4/1998 | Forman et al. |
| 5,747,064 A | 5/1998 | Burnett et al. |
| 5,759,570 A | 6/1998 | Arnold |
| 5,769,608 A | 6/1998 | Seale |
| 5,776,098 A | 7/1998 | Silver et al. |
| 5,776,193 A | 7/1998 | Kwan et al. |
| 5,779,657 A | 7/1998 | Daneshvar |
| 5,785,508 A | 7/1998 | Bolt |

(56) References Cited

U.S. PATENT DOCUMENTS

| | | | |
|---|---|---|---|
| 5,785,688 A | 7/1998 | Joshi et al. | |
| 5,817,145 A | 10/1998 | Augustine et al. | |
| 5,830,496 A | 11/1998 | Freeman | |
| 5,833,646 A | 11/1998 | Masini | |
| 5,834,007 A | 11/1998 | Kubota | |
| 5,843,011 A | 12/1998 | Lucas | |
| 5,852,126 A | 12/1998 | Barnard et al. | |
| 5,863,184 A | 1/1999 | Juterbock et al. | |
| 5,868,933 A | 2/1999 | Patrick et al. | |
| 5,874,500 A | 2/1999 | Rhee et al. | |
| 5,876,611 A | 3/1999 | Shettigar | |
| 5,897,296 A | 4/1999 | Yamamoto et al. | |
| 5,902,256 A | 5/1999 | Benaron | |
| 5,902,260 A * | 5/1999 | Gilman | A61F 13/025 |
| | | | 602/41 |
| 5,904,659 A | 5/1999 | Duarte | |
| 5,928,265 A | 7/1999 | Fleischmann | |
| 5,941,840 A | 8/1999 | Court et al. | |
| 5,945,115 A | 8/1999 | Dunn et al. | |
| 5,950,523 A | 9/1999 | Reynolds | |
| 5,962,010 A | 10/1999 | Greff et al. | |
| 5,964,723 A | 10/1999 | Augustine | |
| 5,998,472 A | 12/1999 | Berger et al. | |
| 6,010,527 A | 1/2000 | Augustine et al. | |
| 6,013,097 A | 1/2000 | Augustine et al. | |
| 6,068,588 A | 5/2000 | Goldowsky | |
| 6,071,267 A | 6/2000 | Zamierowski | |
| 6,080,685 A | 6/2000 | Eady | |
| 6,093,160 A | 7/2000 | Augustine et al. | |
| 6,102,680 A | 8/2000 | Fraser et al. | |
| 6,103,951 A | 8/2000 | Freeman | |
| 6,110,197 A | 8/2000 | Augustine et al. | |
| 6,117,111 A | 9/2000 | Fleischmann | |
| 6,135,116 A | 10/2000 | Vogel et al. | |
| 6,138,550 A | 10/2000 | Fingar, Jr. | |
| 6,142,982 A | 11/2000 | Hunt et al. | |
| 6,143,352 A | 11/2000 | Clark et al. | |
| 6,145,430 A | 11/2000 | Able et al. | |
| 6,158,327 A | 12/2000 | Huss | |
| 6,162,194 A | 12/2000 | Shipp | |
| 6,165,201 A | 12/2000 | Sawhney et al. | |
| 6,168,788 B1 | 1/2001 | Wortham | |
| 6,168,800 B1 | 1/2001 | Dobos et al. | |
| 6,176,307 B1 | 1/2001 | Danos et al. | |
| 6,183,438 B1 | 2/2001 | Berguer | |
| 6,214,332 B1 | 4/2001 | Askill et al. | |
| 6,225,523 B1 | 5/2001 | Masini | |
| 6,227,825 B1 | 5/2001 | Vay | |
| 6,230,609 B1 | 5/2001 | Fingar | |
| 6,231,310 B1 | 5/2001 | Tojo et al. | |
| 6,248,084 B1 | 6/2001 | Augustine et al. | |
| 6,249,198 B1 | 6/2001 | Clark et al. | |
| 6,252,129 B1 | 6/2001 | Coffee | |
| 6,254,567 B1 | 7/2001 | Treu et al. | |
| 6,255,552 B1 | 7/2001 | Cummings et al. | |
| 6,257,847 B1 | 7/2001 | Silver et al. | |
| 6,261,276 B1 | 7/2001 | Reitsma | |
| 6,261,283 B1 | 7/2001 | Morgan et al. | |
| 6,267,740 B1 | 7/2001 | Augustine et al. | |
| 6,287,521 B1 | 9/2001 | Quay et al. | |
| 6,291,050 B1 | 9/2001 | Cree et al. | |
| 6,293,917 B1 | 9/2001 | Augustine et al. | |
| 6,323,568 B1 | 11/2001 | Zabar | |
| 6,327,960 B1 | 12/2001 | Heimueller et al. | |
| 6,343,539 B1 | 2/2002 | Du | |
| 6,345,623 B1 | 2/2002 | Heaton et al. | |
| 6,383,163 B1 | 5/2002 | Kelly et al. | |
| 6,391,294 B1 | 5/2002 | Dettmar et al. | |
| 6,398,761 B1 | 6/2002 | Bills et al. | |
| 6,398,767 B1 | 6/2002 | Fleischmann | |
| 6,402,724 B1 | 6/2002 | Smith et al. | |
| 6,413,057 B1 | 7/2002 | Hong et al. | |
| 6,440,167 B2 | 8/2002 | Shimizu | |
| 6,447,802 B2 | 9/2002 | Sessions et al. | |
| 6,450,773 B1 | 9/2002 | Upton | |
| 6,458,109 B1 | 10/2002 | Henley et al. | |
| 6,465,708 B1 | 10/2002 | Augustine | |
| 6,468,295 B2 | 10/2002 | Augustine et al. | |
| 6,471,685 B1 | 10/2002 | Johnson | |
| 6,471,982 B1 | 10/2002 | Lydon et al. | |
| 6,481,986 B1 | 11/2002 | Silver et al. | |
| 6,486,285 B2 | 11/2002 | Fujita | |
| 6,491,684 B1 | 12/2002 | Joshi et al. | |
| 6,495,127 B1 | 12/2002 | Wallace et al. | |
| 6,500,112 B1 | 12/2002 | Khouri | |
| 6,509,031 B1 | 1/2003 | Miller et al. | |
| 6,521,251 B2 | 2/2003 | Askill et al. | |
| 6,540,490 B1 | 4/2003 | Lilie | |
| 6,547,467 B2 | 4/2003 | Quintero | |
| 6,547,756 B1 | 4/2003 | Greter et al. | |
| 6,553,998 B2 | 4/2003 | Heaton et al. | |
| 6,575,940 B1 | 6/2003 | Levinson et al. | |
| 6,580,012 B1 | 6/2003 | Augustine et al. | |
| 6,589,028 B1 | 7/2003 | Eckerbom et al. | |
| 6,596,704 B1 | 7/2003 | Court et al. | |
| 6,599,262 B1 | 7/2003 | Masini | |
| 6,607,495 B1 | 8/2003 | Skalak et al. | |
| 6,626,891 B2 | 9/2003 | Ohmstede | |
| 6,627,216 B2 | 9/2003 | Brandt et al. | |
| 6,629,774 B1 | 10/2003 | Guruendeman | |
| 6,638,035 B1 | 10/2003 | Puff | |
| 6,638,270 B2 | 10/2003 | Johnson | |
| 6,648,862 B2 | 11/2003 | Watson | |
| 6,655,257 B1 | 12/2003 | Meyer | |
| 6,673,028 B1 | 1/2004 | Argenta et al. | |
| 6,673,036 B1 | 1/2004 | Britto | |
| 6,676,610 B2 | 1/2004 | Morton et al. | |
| 6,676,631 B1 | 1/2004 | Grefer | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,699,213 B1 | 3/2004 | Annis et al. | |
| 6,730,299 B1 | 5/2004 | Tayot et al. | |
| 6,752,794 B2 | 6/2004 | Lockwood et al. | |
| 6,755,807 B2 | 6/2004 | Risk et al. | |
| 6,764,462 B2 | 7/2004 | Risk, Jr. et al. | |
| 6,767,334 B1 | 7/2004 | Randolph | |
| 6,775,807 B2 | 8/2004 | Lowther et al. | |
| 6,787,682 B2 | 9/2004 | Gilman | |
| 6,790,438 B1 | 9/2004 | Constancis et al. | |
| 6,794,554 B2 | 9/2004 | Sessions et al. | |
| 6,800,074 B2 | 10/2004 | Henley et al. | |
| 6,808,517 B2 | 10/2004 | Greter et al. | |
| 6,814,079 B2 | 11/2004 | Heaton et al. | |
| 6,823,905 B1 | 11/2004 | Smith et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,936,037 B2 | 8/2005 | Bubb et al. | |
| 6,942,633 B2 | 9/2005 | Odland | |
| 6,951,553 B2 | 10/2005 | Bubb et al. | |
| 6,960,179 B2 | 11/2005 | Gura | |
| 6,977,323 B1 | 12/2005 | Swenson | |
| 6,979,324 B2 | 12/2005 | Bybordi et al. | |
| 6,987,209 B2 | 1/2006 | Augustine et al. | |
| 6,994,702 B1 | 2/2006 | Johnson | |
| 6,997,897 B1 | 2/2006 | Silver et al. | |
| 7,004,915 B2 | 2/2006 | Boynton et al. | |
| 7,008,400 B2 | 3/2006 | Silver et al. | |
| 7,022,113 B2 | 4/2006 | Lockwood et al. | |
| 7,041,057 B1 | 5/2006 | Faupel et al. | |
| 7,067,709 B2 | 6/2006 | Murate et al. | |
| 7,070,584 B2 | 7/2006 | Johnson et al. | |
| 7,077,832 B2 | 7/2006 | Fleischmann | |
| 7,087,806 B2 | 8/2006 | Scheinberg et al. | |
| 7,108,683 B2 | 9/2006 | Zamierowski | |
| 7,117,869 B2 | 10/2006 | Heaton et al. | |
| 7,122,046 B2 | 10/2006 | Augustine et al. | |
| 7,128,735 B2 | 10/2006 | Weston | |
| 7,129,210 B2 | 10/2006 | Lowinger et al. | |
| 7,141,714 B2 | 11/2006 | Nielsen | |
| 7,151,348 B1 | 12/2006 | Ueda et al. | |
| 7,182,085 B1 * | 2/2007 | Larsen | A61F 13/0203 |
| | | | 128/846 |

(56) References Cited

U.S. PATENT DOCUMENTS

| | | |
|---|---|---|
| 7,195,624 B2 | 3/2007 | Lockwood |
| 7,198,046 B1 | 4/2007 | Argenta et al. |
| 7,214,202 B1 | 5/2007 | Vogel et al. |
| 7,216,651 B2 | 5/2007 | Argenta et al. |
| 7,220,889 B2 | 5/2007 | Sigurjonsson et al. |
| 7,238,850 B2 | 7/2007 | Shimanuki |
| 7,255,681 B1 | 8/2007 | Silver et al. |
| 7,273,054 B2 | 9/2007 | Heaton et al. |
| 7,279,612 B1 | 10/2007 | Heaton et al. |
| 7,303,757 B2 | 12/2007 | Schankereli et al. |
| 7,316,672 B1 | 1/2008 | Hunt et al. |
| 7,335,809 B2 | 2/2008 | Riesinger |
| 7,338,482 B2 | 3/2008 | Lockwood et al. |
| 7,361,184 B2 | 4/2008 | Joshi |
| 7,381,211 B2 | 6/2008 | Zamierowski |
| 7,381,859 B2 | 6/2008 | Hunt et al. |
| 7,438,705 B2 | 10/2008 | Karpowicz et al. |
| 7,447,327 B2 | 11/2008 | Kitamura et al. |
| 7,470,830 B2 | 12/2008 | Sigurjonsson et al. |
| 7,485,112 B2 | 2/2009 | Karpowicz et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood |
| 7,553,306 B1 | 6/2009 | Hunt et al. |
| 7,569,742 B2 | 8/2009 | Haggstrom et al. |
| 7,601,129 B2 | 10/2009 | Aali |
| 7,605,298 B2 | 10/2009 | Bechert et al. |
| 7,611,500 B1 | 11/2009 | Lina et al. |
| 7,612,247 B2 | 11/2009 | Oyaski |
| 7,615,036 B2 | 11/2009 | Joshi et al. |
| 7,622,629 B2 | 11/2009 | Aali |
| D605,775 S | 12/2009 | Koch et al. |
| 7,625,362 B2 | 12/2009 | Boehringer et al. |
| D608,007 S | 1/2010 | Arbesman et al. |
| 7,645,253 B2 | 1/2010 | Gura et al. |
| 7,645,269 B2 | 1/2010 | Zamierowski |
| 7,670,323 B2 | 3/2010 | Hunt et al. |
| 7,678,090 B2 | 3/2010 | Risk, Jr. |
| 7,687,678 B2 | 3/2010 | Jacobs |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,718,249 B2 | 5/2010 | Russell et al. |
| 7,722,582 B2 | 5/2010 | Lina et al. |
| 7,731,702 B2 | 6/2010 | Bybordi et al. |
| 7,745,681 B1 | 6/2010 | Ferguson |
| 7,749,531 B2 | 7/2010 | Booher |
| 7,753,894 B2 | 7/2010 | Blott et al. |
| 7,754,936 B2 | 7/2010 | Heaton et al. |
| 7,754,937 B2 | 7/2010 | Boehringer et al. |
| 7,758,514 B2 | 7/2010 | Grigoryants et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,763,769 B2 | 7/2010 | Johnson et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,339 B2 | 1/2011 | Mulligan |
| 7,862,831 B2 | 1/2011 | Wang et al. |
| 7,867,206 B2 | 1/2011 | Lockwood et al. |
| 7,880,050 B2 | 2/2011 | Robinson et al. |
| 7,884,258 B2 | 2/2011 | Boehringer et al. |
| 7,886,746 B2 | 2/2011 | Heaton et al. |
| 7,896,823 B2 | 3/2011 | Mangrum et al. |
| 7,896,856 B2 | 3/2011 | Petrosenko et al. |
| 7,896,864 B2 | 3/2011 | Lockwood et al. |
| 7,909,805 B2 | 3/2011 | Weston |
| 7,910,135 B2 | 3/2011 | St. John et al. |
| 7,910,791 B2 | 3/2011 | Coffey |
| 7,922,676 B2 | 4/2011 | Daskal et al. |
| 7,922,703 B2 | 4/2011 | Riesinger |
| 7,927,318 B2 | 4/2011 | Risk, Jr. et al. |
| 7,931,630 B2 | 4/2011 | Nishtala et al. |
| 7,942,866 B2 | 5/2011 | Radi et al. |
| 7,951,100 B2 | 5/2011 | Hunt et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,988,680 B2 | 8/2011 | Lockwood et al. |
| 7,998,125 B2 | 8/2011 | Weston |
| 8,007,164 B2 | 8/2011 | Miyano et al. |
| 8,007,257 B2 | 8/2011 | Heaton et al. |
| 8,007,481 B2 | 8/2011 | Schuessler et al. |
| 8,021,348 B2 | 9/2011 | Risk, Jr. et al. |
| 8,022,266 B2 | 9/2011 | Boehringer et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,273 B2 | 11/2011 | Weston |
| 8,062,331 B2 | 11/2011 | Zamierowski |
| 8,080,702 B2 | 12/2011 | Blott et al. |
| 8,084,663 B2 | 12/2011 | Watson, Jr. |
| 8,092,441 B2 | 1/2012 | Sugito |
| 8,097,272 B2 | 1/2012 | Addison |
| 8,100,887 B2 | 1/2012 | Weston et al. |
| 8,105,295 B2 | 1/2012 | Blott et al. |
| 8,118,794 B2 | 2/2012 | Weston et al. |
| 8,119,160 B2 | 2/2012 | Looney et al. |
| 8,133,211 B2 | 3/2012 | Cavanaugh, II et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,168,848 B2 | 5/2012 | Lockwood et al. |
| 8,192,409 B2 | 6/2012 | Hardman et al. |
| 8,207,392 B2 | 6/2012 | Haggstrom et al. |
| 8,211,071 B2 | 7/2012 | Mormino et al. |
| 8,212,100 B2 | 7/2012 | Moore |
| 8,215,929 B2 | 7/2012 | Shen et al. |
| 8,226,942 B2 | 7/2012 | Charier et al. |
| 8,235,955 B2 | 8/2012 | Blott et al. |
| 8,235,972 B2 | 8/2012 | Adahan |
| 8,241,015 B2 | 8/2012 | Lillie |
| 8,241,261 B2 | 8/2012 | Randolph et al. |
| 8,246,606 B2 | 8/2012 | Stevenson et al. |
| 8,251,979 B2 | 8/2012 | Malhi |
| 8,257,327 B2 | 9/2012 | Blott et al. |
| 8,257,328 B2 | 9/2012 | Augustine et al. |
| 8,267,908 B2 | 9/2012 | Coulthard |
| 8,267,918 B2 | 9/2012 | Johnson et al. |
| 8,273,368 B2 | 9/2012 | Ambrosio et al. |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,317,774 B2 | 11/2012 | Adahan |
| 8,323,264 B2 | 12/2012 | Weston et al. |
| 8,338,402 B2 | 12/2012 | Fry et al. |
| 8,348,910 B2 | 1/2013 | Blott et al. |

(56) References Cited

U.S. PATENT DOCUMENTS

| | | |
|---|---|---|
| 8,372,049 B2 | 2/2013 | Jaeb et al. |
| 8,372,050 B2 | 2/2013 | Jaeb et al. |
| 8,376,972 B2 | 2/2013 | Fleischmann |
| 8,382,731 B2 | 2/2013 | Johannison |
| 8,404,921 B2 | 3/2013 | Lee et al. |
| D679,819 S | 4/2013 | Peron |
| D679,820 S | 4/2013 | Peron |
| 8,410,189 B2 | 4/2013 | Carnahan et al. |
| 8,414,519 B2 | 4/2013 | Hudspeth et al. |
| 8,419,696 B2 | 4/2013 | Wilkes |
| 8,425,478 B2 | 4/2013 | Olson |
| 8,444,612 B2 | 5/2013 | Patel et al. |
| 8,460,255 B2 | 6/2013 | Joshi et al. |
| 8,494,349 B2 | 7/2013 | Gordon |
| 8,506,554 B2 | 8/2013 | Adahan |
| 8,529,548 B2 | 9/2013 | Blott et al. |
| 8,535,283 B2 | 9/2013 | Heaton et al. |
| 8,535,296 B2 | 9/2013 | Blott et al. |
| 8,545,464 B2 | 10/2013 | Weston |
| 8,545,466 B2 | 10/2013 | Andresen et al. |
| 8,556,871 B2 | 10/2013 | Mormino et al. |
| 8,569,566 B2 | 10/2013 | Blott et al. |
| 8,603,074 B2 | 12/2013 | Kagan |
| 8,617,129 B2 | 12/2013 | Hartwell |
| 8,622,981 B2 | 1/2014 | Hartwell et al. |
| 8,628,505 B2 | 1/2014 | Weston |
| 8,641,691 B2 | 2/2014 | Fink |
| 8,663,198 B2 | 3/2014 | Buan et al. |
| 8,679,079 B2 | 3/2014 | Heaton et al. |
| 8,715,256 B2 | 5/2014 | Greener |
| 8,753,670 B2 | 6/2014 | Delmotte |
| 8,764,732 B2 | 7/2014 | Hartwell |
| 8,795,243 B2 | 8/2014 | Weston |
| 8,795,244 B2 | 8/2014 | Randolph et al. |
| 8,795,635 B2 | 8/2014 | Tamarkin et al. |
| 8,795,713 B2 | 8/2014 | Makower et al. |
| 8,808,274 B2 | 8/2014 | Hartwell |
| 8,814,842 B2 | 8/2014 | Coulthard et al. |
| 8,827,983 B2 | 9/2014 | Braga et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,864,748 B2 | 10/2014 | Coulthard et al. |
| 8,905,985 B2 | 12/2014 | Allen et al. |
| 8,915,895 B2 | 12/2014 | Jaeb et al. |
| 8,945,074 B2 | 2/2015 | Buan et al. |
| 8,956,336 B2 | 2/2015 | Haggstrom et al. |
| 8,968,773 B2 | 3/2015 | Thomas et al. |
| 8,974,429 B2 | 3/2015 | Gordon et al. |
| 9,012,714 B2 | 4/2015 | Fleischmann |
| 9,028,872 B2 | 5/2015 | Gaserod et al. |
| 9,033,942 B2 | 5/2015 | Vess |
| 9,044,579 B2 | 6/2015 | Blott et al. |
| 9,050,209 B2 | 6/2015 | Coulthard et al. |
| 9,061,095 B2 | 6/2015 | Adie et al. |
| 9,084,845 B2 | 7/2015 | Adie et al. |
| 9,127,665 B2 | 9/2015 | Locke et al. |
| 9,168,330 B2 | 10/2015 | Joshi et al. |
| 9,198,802 B2 | 12/2015 | Robinson et al. |
| 9,199,012 B2 | 12/2015 | Vitaris et al. |
| 9,211,365 B2 | 12/2015 | Weston |
| 9,220,822 B2 | 12/2015 | Hartwell et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,414,968 B2 | 8/2016 | Heagle |
| 9,421,133 B2 | 8/2016 | Hu et al. |
| 9,446,178 B2 | 9/2016 | Blott et al. |
| 9,452,245 B2 | 9/2016 | Jaeb et al. |
| 9,452,248 B2 | 9/2016 | Blott et al. |
| 9,456,928 B2 | 10/2016 | Haggstrom et al. |
| 9,669,138 B2 | 6/2017 | Joshi et al. |
| 9,795,725 B2 | 10/2017 | Joshi et al. |
| 9,844,475 B2 | 12/2017 | Hartwell |
| 10,010,656 B2 | 7/2018 | Jaeb et al. |
| 10,123,909 B2 | 11/2018 | Hartwell |
| 10,265,445 B2 | 4/2019 | Weston |
| 10,384,041 B2 | 8/2019 | Patel et al. |
| 10,391,212 B2 | 8/2019 | Joshi et al. |
| 10,463,773 B2 | 11/2019 | Haggstrom et al. |
| 2001/0001278 A1 | 5/2001 | Drevet |
| 2001/0004082 A1 | 6/2001 | Keller et al. |
| 2001/0031911 A1 | 10/2001 | Khouri |
| 2001/0033795 A1 | 10/2001 | Humpheries |
| 2001/0034499 A1 | 10/2001 | Sessions et al. |
| 2001/0038799 A1 | 11/2001 | Silver et al. |
| 2001/0043870 A1 | 11/2001 | Song |
| 2001/0043913 A1 | 11/2001 | Spaans et al. |
| 2001/0043943 A1 | 11/2001 | Coffey |
| 2002/0002209 A1 | 1/2002 | Mork |
| 2002/0017304 A1 | 2/2002 | Heaton et al. |
| 2002/0026133 A1 | 2/2002 | Augustine et al. |
| 2002/0026946 A1 | 3/2002 | McKay |
| 2002/0038826 A1 | 4/2002 | Hurray et al. |
| 2002/0082567 A1 | 6/2002 | Lockwood et al. |
| 2002/0122732 A1 | 9/2002 | Oh et al. |
| 2002/0122771 A1 | 9/2002 | Holland et al. |
| 2002/0138036 A1 | 9/2002 | Babaev |
| 2002/0143286 A1 | 10/2002 | Tumey |
| 2002/0145007 A1 | 10/2002 | Sawhney et al. |
| 2002/0161317 A1 | 10/2002 | Risk et al. |
| 2002/0164255 A1 | 11/2002 | Burr et al. |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2002/0198504 A1 | 12/2002 | Risk et al. |
| 2003/0021775 A1 | 1/2003 | Freeman |
| 2003/0023286 A1 | 1/2003 | Augustine et al. |
| 2003/0035743 A1 | 2/2003 | Lee et al. |
| 2003/0040478 A1 | 2/2003 | Drucker et al. |
| 2003/0045825 A1 | 3/2003 | Etheredge, III |
| 2003/0064190 A1* | 4/2003 | Carte ............. A61F 13/023 428/40.1 |
| 2003/0069529 A1 | 4/2003 | Augustine et al. |
| 2003/0069535 A1 | 4/2003 | Shalaby |
| 2003/0069536 A1 | 4/2003 | Greter et al. |
| 2003/0069563 A1 | 4/2003 | Johnson |
| 2003/0088202 A1* | 5/2003 | Gilman ............. A61F 13/023 602/46 |
| 2003/0095879 A1 | 5/2003 | Oh et al. |
| 2003/0099558 A1 | 5/2003 | Chang |
| 2003/0108430 A1 | 6/2003 | Yoshida et al. |
| 2003/0110939 A1 | 6/2003 | Able et al. |
| 2003/0125646 A1 | 7/2003 | Whitlock |
| 2003/0125649 A1 | 7/2003 | Mcintosh et al. |
| 2003/0133812 A1 | 7/2003 | Puff et al. |
| 2003/0143189 A1 | 7/2003 | Askill et al. |
| 2003/0144619 A1 | 7/2003 | Augustine |
| 2003/0153860 A1 | 8/2003 | Nielsen et al. |
| 2003/0161735 A1 | 8/2003 | Kim et al. |
| 2003/0171675 A1 | 9/2003 | Rosenberg |
| 2003/0175125 A1 | 9/2003 | Kwon et al. |
| 2003/0175135 A1 | 9/2003 | Heo et al. |
| 2003/0175798 A1 | 9/2003 | Raees et al. |
| 2003/0183653 A1 | 10/2003 | Bills |
| 2003/0188754 A1 | 10/2003 | Heaton et al. |
| 2003/0212357 A1 | 11/2003 | Pace |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2003/0230191 A1 | 12/2003 | Ohrle et al. |
| 2004/0005222 A1 | 1/2004 | Yoshida et al. |
| 2004/0006319 A1 | 1/2004 | Lina et al. |
| 2004/0019342 A1 | 1/2004 | Nagasuna et al. |
| 2004/0024351 A1 | 2/2004 | Greter et al. |
| 2004/0033466 A1 | 2/2004 | Shellard et al. |
| 2004/0037897 A1 | 2/2004 | Benjamin et al. |
| 2004/0039391 A1 | 2/2004 | Argenta et al. |
| 2004/0049187 A1 | 3/2004 | Burnett et al. |
| 2004/0054338 A1 | 3/2004 | Byordi et al. |
| 2004/0057855 A1 | 3/2004 | Gerlach et al. |
| 2004/0064111 A1 | 4/2004 | Lockwood et al. |

(56) References Cited

U.S. PATENT DOCUMENTS

| | | |
|---|---|---|
| 2004/0064132 A1 | 4/2004 | Boehringer et al. |
| 2004/0066097 A1 | 4/2004 | Kobayashi et al. |
| 2004/0071568 A1 | 4/2004 | Hyeon |
| 2004/0071572 A1 | 4/2004 | Greter et al. |
| 2004/0073152 A1 | 4/2004 | Karason et al. |
| 2004/0076662 A1 | 4/2004 | Riesinger |
| 2004/0087884 A1 | 5/2004 | Haddock et al. |
| 2004/0115076 A1 | 6/2004 | Lilie et al. |
| 2004/0118460 A1 | 6/2004 | Stinson |
| 2004/0122434 A1 | 6/2004 | Argenta et al. |
| 2004/0126250 A1 | 7/2004 | Tsuchiya et al. |
| 2004/0126413 A1* | 7/2004 | Sigurjonsson ............ A61L 15/26 424/445 |
| 2004/0127862 A1 | 7/2004 | Bubb et al. |
| 2004/0127863 A1 | 7/2004 | Bubb et al. |
| 2004/0156730 A1 | 8/2004 | Lilie et al. |
| 2004/0163713 A1 | 8/2004 | Schulze et al. |
| 2004/0167482 A1 | 8/2004 | Watson |
| 2004/0167617 A1 | 8/2004 | Voellmicke et al. |
| 2004/0171976 A1 | 9/2004 | Johson |
| 2004/0171998 A1 | 9/2004 | Marasco, Jr. |
| 2004/0182237 A1 | 9/2004 | Headley et al. |
| 2004/0189103 A1 | 9/2004 | Duncan et al. |
| 2004/0241214 A1 | 12/2004 | Kirkwood et al. |
| 2004/0249353 A1 | 12/2004 | Risk, Jr. et al. |
| 2005/0012616 A1 | 1/2005 | Forster et al. |
| 2005/0013957 A1* | 1/2005 | Leschinsky ............. B32B 33/00 428/40.1 |
| 2005/0020955 A1 | 1/2005 | Sanders et al. |
| 2005/0031470 A1 | 2/2005 | Lee |
| 2005/0045461 A1 | 3/2005 | Sweetland et al. |
| 2005/0065471 A1 | 3/2005 | Kuntz |
| 2005/0080372 A1* | 4/2005 | Nielsen ............... A61F 13/0203 602/42 |
| 2005/0085768 A1 | 4/2005 | Greter et al. |
| 2005/0090787 A1 | 4/2005 | Risk et al. |
| 2005/0098031 A1 | 5/2005 | Yoon et al. |
| 2005/0110190 A1 | 5/2005 | Giardini |
| 2005/0111987 A1 | 5/2005 | Yoo et al. |
| 2005/0119737 A1 | 6/2005 | Bene et al. |
| 2005/0123422 A1 | 6/2005 | Lilie |
| 2005/0124966 A1 | 6/2005 | Karpowicz et al. |
| 2005/0129540 A1 | 6/2005 | Puff |
| 2005/0131327 A1 | 6/2005 | Lockwood et al. |
| 2005/0135946 A1 | 6/2005 | Kang et al. |
| 2005/0137539 A1 | 6/2005 | Biggie et al. |
| 2005/0142007 A1 | 6/2005 | Lee et al. |
| 2005/0142008 A1 | 6/2005 | Jung et al. |
| 2005/0155657 A1 | 7/2005 | Kack et al. |
| 2005/0163635 A1 | 7/2005 | Berwanger et al. |
| 2005/0165350 A1 | 7/2005 | Greter et al. |
| 2005/0209560 A1 | 9/2005 | Boukhny et al. |
| 2005/0228329 A1 | 10/2005 | Boehringer et al. |
| 2005/0230422 A1 | 10/2005 | Muller et al. |
| 2005/0245850 A1 | 11/2005 | Freyre et al. |
| 2005/0251117 A1 | 11/2005 | Anderson et al. |
| 2005/0271526 A1 | 12/2005 | Chang et al. |
| 2005/0272142 A1 | 12/2005 | Horita |
| 2005/0276706 A1 | 12/2005 | Radue |
| 2005/0283105 A1 | 12/2005 | Heaton et al. |
| 2006/0009744 A1 | 1/2006 | Edrman et al. |
| 2006/0017332 A1 | 1/2006 | Kang et al. |
| 2006/0018771 A1 | 1/2006 | Song et al. |
| 2006/0019144 A1 | 1/2006 | Hidaka et al. |
| 2006/0024181 A1 | 2/2006 | Kim |
| 2006/0029650 A1 | 2/2006 | Coffey |
| 2006/0029675 A1 | 2/2006 | Ginther |
| 2006/0039806 A1 | 2/2006 | Becker |
| 2006/0056979 A1 | 3/2006 | Yoo et al. |
| 2006/0056980 A1 | 3/2006 | Yoo et al. |
| 2006/0057000 A1 | 3/2006 | Hyeon |
| 2006/0061024 A1 | 3/2006 | Jung et al. |
| 2006/0069365 A1 | 3/2006 | Sperl et al. |
| 2006/0070458 A1 | 4/2006 | Jones et al. |
| 2006/0073036 A1 | 4/2006 | Debrito et al. |
| 2006/0079599 A1 | 4/2006 | Arthur |
| 2006/0086598 A1 | 4/2006 | Sneek et al. |
| 2006/0107642 A1 | 5/2006 | Smith et al. |
| 2006/0110259 A1 | 5/2006 | Puff et al. |
| 2006/0118190 A1 | 6/2006 | Takehana et al. |
| 2006/0122558 A1 | 6/2006 | Sherman et al. |
| 2006/0149170 A1 | 7/2006 | Boynton et al. |
| 2006/0173514 A1 | 8/2006 | Biel et al. |
| 2006/0191575 A1 | 8/2006 | Naesje |
| 2006/0192259 A1 | 8/2006 | Silverbrook |
| 2006/0210411 A1 | 9/2006 | Hyeon |
| 2006/0213527 A1 | 9/2006 | Argenta et al. |
| 2006/0216165 A1 | 9/2006 | Lee |
| 2006/0222532 A1 | 10/2006 | Lee et al. |
| 2006/0228224 A1 | 10/2006 | Hong et al. |
| 2006/0245947 A1 | 11/2006 | Seto et al. |
| 2006/0251523 A1 | 11/2006 | Lee et al. |
| 2006/0253082 A1 | 11/2006 | Mcintosh et al. |
| 2006/0259102 A1 | 11/2006 | Slatkine |
| 2006/0273109 A1 | 12/2006 | Keller |
| 2006/0282028 A1 | 12/2006 | Howard et al. |
| 2006/0282174 A1 | 12/2006 | Haines |
| 2006/0287632 A1 | 12/2006 | Sarangapani |
| 2007/0004896 A1 | 1/2007 | Ito et al. |
| 2007/0005028 A1 | 1/2007 | Risk et al. |
| 2007/0009580 A1 | 1/2007 | DiCosmo et al. |
| 2007/0016152 A1 | 1/2007 | Karpowicz et al. |
| 2007/0021697 A1 | 1/2007 | Ginther et al. |
| 2007/0032741 A1 | 2/2007 | Hibner et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0040454 A1 | 2/2007 | Freudenberger et al. |
| 2007/0041856 A1 | 2/2007 | Hansen et al. |
| 2007/0055209 A1 | 3/2007 | Patel et al. |
| 2007/0078444 A1 | 4/2007 | Larsson |
| 2007/0091614 A1 | 4/2007 | Kaisser et al. |
| 2007/0128055 A1 | 6/2007 | Lee |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0179460 A1 | 8/2007 | Adahan |
| 2007/0185463 A1 | 8/2007 | Mulligan |
| 2007/0196214 A1 | 8/2007 | Bocchiola |
| 2007/0203062 A1 | 8/2007 | Ellis-Behnke et al. |
| 2007/0219513 A1 | 9/2007 | Lina et al. |
| 2007/0225663 A1 | 9/2007 | Watt et al. |
| 2007/0255187 A1 | 11/2007 | Branch |
| 2007/0256428 A1 | 11/2007 | Unger et al. |
| 2007/0260207 A1 | 11/2007 | Ugander et al. |
| 2007/0260226 A1 | 11/2007 | Jaeb et al. |
| 2007/0265586 A1* | 11/2007 | Joshi .................. A61F 13/0216 604/313 |
| 2007/0276195 A1 | 11/2007 | Xu et al. |
| 2007/0276309 A1 | 11/2007 | Xu et al. |
| 2007/0282283 A1 | 12/2007 | Kaern et al. |
| 2007/0295201 A1 | 12/2007 | Dadd |
| 2008/0004549 A1 | 1/2008 | Anderson et al. |
| 2008/0009812 A1 | 1/2008 | Riesinger |
| 2008/0015526 A1 | 1/2008 | Reiner et al. |
| 2008/0020178 A1 | 1/2008 | Oehrle et al. |
| 2008/0021356 A1 | 1/2008 | Castello Escude et al. |
| 2008/0031748 A1 | 2/2008 | Ihle et al. |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0051708 A1 | 2/2008 | Kumar et al. |
| 2008/0051716 A1 | 2/2008 | Stutz |
| 2008/0060550 A1 | 3/2008 | MacDonald et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2008/0082040 A1 | 4/2008 | Kubler et al. |
| 2008/0089173 A1 | 4/2008 | Lu et al. |
| 2008/0094753 A1 | 4/2008 | Brodkin et al. |
| 2008/0110336 A1 | 5/2008 | Bovill et al. |
| 2008/0125697 A1 | 5/2008 | Gao |
| 2008/0125698 A1 | 5/2008 | Gerg et al. |
| 2008/0132821 A1 | 6/2008 | Propp et al. |

(56) References Cited

U.S. PATENT DOCUMENTS

| | | |
|---|---|---|
| 2008/0200905 A1 | 8/2008 | Heaton |
| 2008/0206155 A1 | 8/2008 | Tamarkin et al. |
| 2008/0208147 A1 | 8/2008 | Argenta et al. |
| 2008/0208163 A1 | 8/2008 | Wilkie |
| 2008/0211435 A1 | 9/2008 | Imagawa |
| 2008/0223378 A1 | 9/2008 | Henderson et al. |
| 2008/0234641 A1 | 9/2008 | Locke et al. |
| 2008/0240942 A1 | 10/2008 | Heinrich et al. |
| 2008/0254103 A1 | 10/2008 | Harris et al. |
| 2008/0260551 A1 | 10/2008 | Simmons |
| 2008/0281281 A1 | 11/2008 | Meyer et al. |
| 2008/0287880 A1 | 11/2008 | Keller |
| 2008/0294147 A1 | 11/2008 | Radl et al. |
| 2008/0300555 A1 | 12/2008 | Olson et al. |
| 2008/0306407 A1 | 12/2008 | Taylor |
| 2008/0306456 A1 | 12/2008 | Riesinger |
| 2008/0310980 A1 | 12/2008 | Ramsdorf et al. |
| 2008/0312572 A1 | 12/2008 | Riesinger |
| 2008/0312613 A1 | 12/2008 | Heaton et al. |
| 2008/0314929 A1 | 12/2008 | Keller |
| 2009/0005746 A1 | 1/2009 | Nielsen et al. |
| 2009/0012484 A1 | 1/2009 | Nielsen et al. |
| 2009/0020561 A1 | 1/2009 | Keller |
| 2009/0022779 A1 | 1/2009 | Kelly et al. |
| 2009/0028733 A1 | 1/2009 | Duwel |
| 2009/0030086 A1 | 1/2009 | Eady et al. |
| 2009/0036873 A1 | 2/2009 | Nielsen et al. |
| 2009/0048556 A1 | 2/2009 | Durand |
| 2009/0053081 A1 | 2/2009 | Griffiths |
| 2009/0054855 A1 | 2/2009 | Blott et al. |
| 2009/0071551 A1 | 3/2009 | Chalich |
| 2009/0081049 A1 | 3/2009 | Tian et al. |
| 2009/0082740 A1 | 3/2009 | Lockwood et al. |
| 2009/0087323 A1 | 4/2009 | Blakey et al. |
| 2009/0093550 A1 | 4/2009 | Rolfes et al. |
| 2009/0093779 A1 | 4/2009 | Riesinger |
| 2009/0098073 A1 | 4/2009 | MacDonald et al. |
| 2009/0114293 A1 | 5/2009 | Kanai et al. |
| 2009/0125004 A1 | 5/2009 | Shen et al. |
| 2009/0129986 A1 | 5/2009 | Wimberger-Friedl et al. |
| 2009/0131892 A1 | 5/2009 | Karpowicz et al. |
| 2009/0134186 A1 | 5/2009 | Keller |
| 2009/0137973 A1 | 5/2009 | Karpowicz et al. |
| 2009/0149821 A1 | 6/2009 | Scherson et al. |
| 2009/0157017 A1 | 6/2009 | Ambrosio |
| 2009/0157024 A1 | 6/2009 | Song |
| 2009/0166411 A1 | 7/2009 | Kramer et al. |
| 2009/0192467 A1 | 7/2009 | Hansen et al. |
| 2009/0196844 A1 | 8/2009 | Choi et al. |
| 2009/0198201 A1 | 8/2009 | Adahan |
| 2009/0204085 A1 | 8/2009 | Biggie et al. |
| 2009/0206778 A1 | 8/2009 | Roh et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0227969 A1* | 9/2009 | Jaeb .................... A61M 1/0088 604/313 |
| 2009/0234306 A1 | 9/2009 | Vitaris |
| 2009/0254053 A1 | 10/2009 | Svensby et al. |
| 2009/0254066 A1 | 10/2009 | Heaton |
| 2009/0259203 A1 | 10/2009 | Hu et al. |
| 2009/0264807 A1 | 10/2009 | Haggstrom et al. |
| 2009/0270820 A1 | 10/2009 | Johnson |
| 2009/0275872 A1 | 11/2009 | Addison et al. |
| 2009/0275922 A1 | 11/2009 | Coulthard et al. |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0299306 A1 | 12/2009 | Buan |
| 2009/0304534 A1 | 12/2009 | Richter |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0022990 A1 | 1/2010 | Karpowicz et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036305 A1 | 2/2010 | Green |
| 2010/0036334 A1 | 2/2010 | Heagle et al. |
| 2010/0042059 A1 | 2/2010 | Pratt et al. |
| 2010/0068820 A1 | 3/2010 | Meathrel et al. |
| 2010/0069829 A1 | 3/2010 | Hutchinson et al. |
| 2010/0069850 A1 | 3/2010 | Fabo |
| 2010/0069858 A1 | 3/2010 | Olson |
| 2010/0069863 A1 | 3/2010 | Olson |
| 2010/0094234 A1 | 4/2010 | Ramella et al. |
| 2010/0098566 A1 | 4/2010 | Kang |
| 2010/0100160 A1 | 4/2010 | Edman et al. |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0145289 A1 | 6/2010 | Line et al. |
| 2010/0150991 A1 | 6/2010 | Bernstein |
| 2010/0159192 A1 | 6/2010 | Cotton |
| 2010/0160878 A1 | 6/2010 | Hunt et al. |
| 2010/0168633 A1* | 7/2010 | Bougherara ........ A61F 13/0283 602/43 |
| 2010/0191178 A1 | 7/2010 | Ross et al. |
| 2010/0191196 A1 | 7/2010 | Heagle |
| 2010/0191198 A1 | 7/2010 | Heagle |
| 2010/0204663 A1 | 8/2010 | Wudyka |
| 2010/0210986 A1 | 8/2010 | Sanders |
| 2010/0211030 A1 | 8/2010 | Turner et al. |
| 2010/0228205 A1 | 9/2010 | Hu et al. |
| 2010/0230467 A1 | 9/2010 | Crisuolo et al. |
| 2010/0244780 A1 | 9/2010 | Turner |
| 2010/0249733 A9 | 9/2010 | Blott et al. |
| 2010/0262090 A1 | 10/2010 | Riesinger |
| 2010/0262091 A1 | 10/2010 | Larsson |
| 2010/0265649 A1 | 10/2010 | Singh et al. |
| 2010/0268176 A1 | 10/2010 | Johnson et al. |
| 2010/0268179 A1 | 10/2010 | Kelch et al. |
| 2010/0280435 A1 | 11/2010 | Raney et al. |
| 2010/0280468 A1 | 11/2010 | Haggstrom et al. |
| 2010/0280469 A1 | 11/2010 | Hall |
| 2010/0286639 A1* | 11/2010 | Scholz ................ A61M 1/0088 604/319 |
| 2010/0292632 A1 | 11/2010 | Mulvihill et al. |
| 2010/0305490 A1 | 12/2010 | Coulthard et al. |
| 2010/0305526 A1 | 12/2010 | Robinson et al. |
| 2010/0318043 A1 | 12/2010 | Malhi et al. |
| 2010/0318052 A1 | 12/2010 | Ha et al. |
| 2010/0318071 A1 | 12/2010 | Wudyka |
| 2011/0000069 A1 | 1/2011 | Ramsdorf et al. |
| 2011/0004172 A1 | 1/2011 | Eckstein et al. |
| 2011/0004173 A1 | 1/2011 | Hu et al. |
| 2011/0015587 A1 | 1/2011 | Tumey et al. |
| 2011/0015593 A1 | 1/2011 | Svedman et al. |
| 2011/0020588 A1 | 1/2011 | Kinugawa et al. |
| 2011/0021431 A1 | 1/2011 | Jones et al. |
| 2011/0022013 A1 | 1/2011 | Boynton et al. |
| 2011/0028290 A1 | 2/2011 | Ozawa |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0033503 A1 | 2/2011 | Sinko et al. |
| 2011/0034869 A1 | 2/2011 | Greter et al. |
| 2011/0034888 A1 | 2/2011 | Aali |
| 2011/0034892 A1 | 2/2011 | Buan |
| 2011/0034894 A1 | 2/2011 | Riesinger |
| 2011/0038741 A1 | 2/2011 | Lissner et al. |
| 2011/0054422 A1 | 3/2011 | Locke et al. |
| 2011/0054423 A1 | 3/2011 | Blott et al. |
| 2011/0071415 A1 | 3/2011 | Karwoski et al. |
| 2011/0081267 A1 | 4/2011 | McCrone et al. |
| 2011/0086077 A1 | 4/2011 | McCrea et al. |
| 2011/0092927 A1 | 4/2011 | Wilkes et al. |
| 2011/0092958 A1 | 4/2011 | Jacobs |
| 2011/0098600 A1 | 4/2011 | Matsumura et al. |
| 2011/0103984 A1 | 5/2011 | Santa |

(56) References Cited

U.S. PATENT DOCUMENTS

| | | |
|---|---|---|
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125066 A1 | 5/2011 | Robinson et al. |
| 2011/0130712 A1 | 6/2011 | Topaz |
| 2011/0171044 A1 | 7/2011 | Flanigan |
| 2011/0172617 A1 | 7/2011 | Riesinger |
| 2011/0176945 A1 | 7/2011 | Drevet |
| 2011/0176946 A1 | 7/2011 | Drevet |
| 2011/0224631 A1 | 9/2011 | Simmons |
| 2011/0229352 A1 | 9/2011 | Herbert |
| 2011/0236265 A1 | 9/2011 | Hasui et al. |
| 2011/0236277 A1 | 9/2011 | Lee et al. |
| 2011/0251569 A1 | 10/2011 | Turner et al. |
| 2011/0257572 A1 | 10/2011 | Locke et al. |
| 2011/0270201 A1 | 11/2011 | Bubb et al. |
| 2011/0270202 A1 | 11/2011 | Boehringer et al. |
| 2011/0295220 A1 | 12/2011 | Heaton et al. |
| 2011/0311379 A1 | 12/2011 | Hale et al. |
| 2011/0313373 A1 | 12/2011 | Riesinger |
| 2011/0313374 A1 | 12/2011 | Lockwood et al. |
| 2012/0000208 A1 | 1/2012 | Hon et al. |
| 2012/0008817 A1 | 1/2012 | Grinker et al. |
| 2012/0046625 A1 | 2/2012 | Johannison |
| 2012/0095380 A1 | 4/2012 | Gergley et al. |
| 2012/0109085 A1 | 5/2012 | McNeil |
| 2012/0130332 A1 | 5/2012 | Cotton et al. |
| 2012/0184930 A1 | 7/2012 | Johannison |
| 2012/0220960 A1 | 8/2012 | Ruland |
| 2012/0251359 A1 | 10/2012 | Neelakantan et al. |
| 2012/0259299 A1 | 10/2012 | Ryu et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2012/0301341 A1 | 11/2012 | Ota et al. |
| 2013/0017110 A1 | 1/2013 | Villagomez et al. |
| 2013/0042753 A1 | 2/2013 | Becker et al. |
| 2013/0085462 A1 | 4/2013 | Nip et al. |
| 2013/0090613 A1 | 4/2013 | Kelch et al. |
| 2013/0090615 A1 | 4/2013 | Jaeb et al. |
| 2013/0102979 A1 | 4/2013 | Coulthard et al. |
| 2013/0118622 A1 | 5/2013 | Patzold et al. |
| 2013/0123755 A1 | 5/2013 | Locke et al. |
| 2013/0138054 A1 | 5/2013 | Fleischmann |
| 2013/0144230 A1 | 6/2013 | Wu et al. |
| 2013/0150814 A1 | 6/2013 | Buan |
| 2013/0165878 A1 | 6/2013 | Heagle |
| 2013/0209277 A1 | 8/2013 | Locke et al. |
| 2013/0209279 A1 | 8/2013 | Locke et al. |
| 2013/0209281 A1 | 8/2013 | Locke et al. |
| 2013/0213506 A1 | 8/2013 | Chen et al. |
| 2013/0223979 A1 | 8/2013 | Locke et al. |
| 2013/0267917 A1 | 10/2013 | Pan et al. |
| 2013/0274688 A1 | 10/2013 | Weston |
| 2013/0280113 A1 | 10/2013 | Miranda et al. |
| 2013/0296762 A1 | 11/2013 | Toth |
| 2013/0331822 A1 | 12/2013 | Patel et al. |
| 2013/0338614 A1 | 12/2013 | Heaton et al. |
| 2013/0340870 A1 | 12/2013 | Ito et al. |
| 2014/0072149 A1 | 3/2014 | Yan et al. |
| 2014/0100516 A1 | 4/2014 | Hunt et al. |
| 2014/0114236 A1 | 4/2014 | Gordon |
| 2014/0114237 A1 | 4/2014 | Gordon |
| 2014/0114268 A1 | 4/2014 | Auguste et al. |
| 2014/0155849 A1 | 6/2014 | Heaton et al. |
| 2014/0163490 A1 | 6/2014 | Locke et al. |
| 2014/0194835 A1 | 7/2014 | Ehlert |
| 2014/0228791 A1 | 8/2014 | Hartwell |
| 2014/0236106 A1 | 8/2014 | Locke et al. |
| 2014/0236109 A1 | 8/2014 | Greener |
| 2014/0276487 A1 | 9/2014 | Locke et al. |
| 2014/0303551 A1 | 10/2014 | Germain et al. |
| 2014/0316359 A1 | 10/2014 | Collinson et al. |
| 2014/0323906 A1 | 10/2014 | Peatfield et al. |
| 2014/0343519 A1 | 11/2014 | Weston |
| 2015/0025482 A1 | 1/2015 | Begin et al. |
| 2015/0032035 A1 | 1/2015 | Banwell et al. |
| 2015/0051560 A1 | 2/2015 | Askem |
| 2015/0065965 A1 | 3/2015 | Haggstrom et al. |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0209492 A1 | 7/2015 | Blott et al. |
| 2015/0258256 A1 | 9/2015 | Jaeb et al. |
| 2015/0250931 A1 | 10/2015 | Bharti et al. |
| 2016/0081859 A1 | 3/2016 | Hartwell |
| 2016/0317357 A1 | 11/2016 | Vitaris et al. |
| 2017/0128642 A1 | 5/2017 | Buan |
| 2017/0181896 A1 | 6/2017 | Hartwell |
| 2017/0266051 A1 | 9/2017 | Hartwell |
| 2018/0133065 A1 | 5/2018 | Hartwell |
| 2018/0214317 A1 | 8/2018 | Hartwell |
| 2018/0235816 A1 | 8/2018 | Hartwell |
| 2018/0243142 A1 | 8/2018 | Hartwell |
| 2018/0311078 A1 | 11/2018 | Hartwell |
| 2019/0142647 A1 | 5/2019 | Hartwell |
| 2019/0224387 A1 | 7/2019 | Weston |
| 2020/0061254 A1 | 2/2020 | Joshi et al. |

FOREIGN PATENT DOCUMENTS

| | | |
|---|---|---|
| DE | 847475 | 8/1952 |
| DE | 3 137 839 | 3/1983 |
| DE | 3 032 092 | 10/1984 |
| DE | 34 43 101 | 5/1986 |
| DE | 3 935 818 | 5/1991 |
| DE | 4 012 232 | 10/1991 |
| DE | 198 44 355 | 4/2000 |
| DE | 20 2004 017 052 | 7/2005 |
| EP | 0 020 662 | 7/1984 |
| EP | 0 208 395 | 1/1987 |
| EP | 0 340 018 | 11/1989 |
| EP | 0 355 186 | 2/1990 |
| EP | 0353972 A1 | 2/1990 |
| EP | 0 512 543 | 11/1992 |
| EP | 0 521 434 | 1/1993 |
| EP | 0 619 105 | 10/1994 |
| EP | 0 759 521 | 2/1997 |
| EP | 0 775 825 | 5/1997 |
| EP | 0 793 019 | 9/1997 |
| EP | 0 809 028 | 11/1997 |
| EP | 0 858 810 | 8/1998 |
| EP | 0 777 504 | 10/1998 |
| EP | 0 888 141 | 1/1999 |
| EP | 0 898 076 | 2/1999 |
| EP | 1 007 015 | 6/2000 |
| EP | 1 013 290 | 6/2000 |
| EP | 1 029 585 | 8/2000 |
| EP | 1 105 171 | 6/2001 |
| EP | 1 105 180 | 6/2001 |
| EP | 1 107 813 | 6/2001 |
| EP | 1 411 874 | 7/2001 |
| EP | 1 030 657 | 10/2001 |
| EP | 1 306 123 | 5/2003 |
| EP | 1 440 737 | 7/2004 |
| EP | 1 449 971 | 8/2004 |
| EP | 1 476 217 | 11/2004 |
| EP | 1 726 276 | 11/2006 |
| EP | 1 923 077 | 11/2006 |
| EP | 1 880 840 | 1/2008 |
| EP | 1 955 887 | 8/2008 |
| EP | 1 985 270 | 10/2008 |
| EP | 1 121 163 | 11/2008 |
| EP | 2 185 206 | 1/2009 |
| EP | 2 178 573 | 2/2009 |
| EP | 2 098 257 | 9/2009 |
| EP | 2 111 804 | 10/2009 |
| EP | 1 985 270 | 12/2009 |
| EP | 2 161 448 | 3/2010 |
| EP | 2 326 295 | 3/2010 |
| EP | 2 216 573 | 8/2010 |
| EP | 2 218 431 | 8/2010 |

(56) References Cited

FOREIGN PATENT DOCUMENTS

| | | |
|---|---|---|
| EP | 2 302 127 A1 | 3/2011 |
| EP | 2 335 749 | 6/2011 |
| EP | 2 349 155 | 8/2011 |
| EP | 1 263 366 | 9/2011 |
| EP | 2 420 214 | 2/2012 |
| EP | 2 021 046 | 3/2012 |
| EP | 2 462 908 | 6/2012 |
| EP | 2 603 699 | 6/2013 |
| EP | 2 305 325 | 4/2014 |
| EP | 2 345 437 | 4/2014 |
| EP | 2 687 245 | 9/2014 |
| EP | 2 544 642 | 1/2015 |
| EP | 2 648 668 | 1/2015 |
| EP | 3 072 542 | 9/2016 |
| EP | 3 062 751 | 8/2017 |
| EP | 3 257 486 | 12/2017 |
| FR | 1 163 907 | 10/1958 |
| FR | 2 939 320 | 6/2010 |
| GB | 114754 | 4/1918 |
| GB | 236350 | 7/1925 |
| GB | 641061 | 8/1950 |
| GB | 1224009 | 3/1971 |
| GB | 1255395 | 12/1971 |
| GB | 1400124 | 7/1975 |
| GB | 1549756 | 8/1979 |
| GB | 2061732 | 5/1981 |
| GB | 2195255 | 4/1988 |
| GB | 2273133 | 6/1994 |
| GB | 2288734 | 11/1995 |
| GB | 2306580 | 5/1997 |
| GB | 2307180 | 5/1997 |
| GB | 2378392 | 2/2003 |
| GB | 2415908 | 1/2006 |
| GB | 2424582 | 10/2006 |
| GB | 2435419 | 2/2007 |
| GB | 2433298 | 3/2007 |
| GB | 2511523 | 9/2014 |
| GB | 0722820 | 7/2019 |
| JP | 59-86824 | 6/1984 |
| JP | 59-87824 | 6/1984 |
| JP | S5986824 U | 6/1984 |
| JP | S5987824 U | 6/1984 |
| JP | S6180018 A | 4/1986 |
| JP | S61-80018 | 5/1986 |
| JP | H04-354722 | 12/1992 |
| JP | 2001-314479 A | 11/2001 |
| JP | 2003-165843 | 6/2003 |
| JP | 2004-000465 | 1/2004 |
| JP | 2005-334188 | 12/2005 |
| RU | 131622 | 8/2013 |
| SU | 1251912 A1 | 4/1983 |
| WO | WO 1983/00742 | 3/1983 |
| WO | WO 1984/01904 | 5/1984 |
| WO | WO 1990/11795 | 10/1990 |
| WO | WO 1991/00718 | 1/1991 |
| WO | WO 1992/009301 | 6/1992 |
| WO | WO 1992/09651 | 6/1992 |
| WO | WO 1992/20299 | 11/1992 |
| WO | WO 1993/06802 | 4/1993 |
| WO | WO 1993/09176 | 5/1993 |
| WO | WO 1994/020133 | 9/1994 |
| WO | WO 1994/21312 | 9/1994 |
| WO | WO 1996/05873 | 2/1996 |
| WO | WO 1996/40174 | 12/1996 |
| WO | WO 1997/03717 | 2/1997 |
| WO | WO 1997/33922 | 9/1997 |
| WO | WO 1997/42986 | 11/1997 |
| WO | WO 1998/03267 | 1/1998 |
| WO | WO 1998/06444 | 2/1998 |
| WO | WO 1999/001173 | 1/1999 |
| WO | WO 1999/17698 | 4/1999 |
| WO | WO 1999/30629 | 6/1999 |
| WO | WO 1999/047097 | 9/1999 |
| WO | WO 1999/65536 | 12/1999 |
| WO | WO 2000/000743 | 1/2000 |
| WO | WO 2000/07653 | 2/2000 |
| WO | WO 2000/38752 | 7/2000 |
| WO | WO 2000/49968 | 8/2000 |
| WO | WO 2000/50143 | 8/2000 |
| WO | WO 2000/56378 | 9/2000 |
| WO | WO 2000/59424 | 10/2000 |
| WO | WO 2000/61206 | 10/2000 |
| WO | WO 2000/62827 | 10/2000 |
| WO | WO 2000/064396 | 11/2000 |
| WO | WO 2000/079154 | 12/2000 |
| WO | WO 2001/19430 | 3/2001 |
| WO | WO 2001/34223 | 5/2001 |
| WO | WO 2001/37922 A2 | 5/2001 |
| WO | WO 2001/37922 A3 | 5/2001 |
| WO | WO 2001/062312 | 8/2001 |
| WO | WO 2001/066017 | 9/2001 |
| WO | WO 2001/85248 | 11/2001 |
| WO | WO 2001/89431 | 11/2001 |
| WO | WO 2002/02079 | 1/2002 |
| WO | WO 2002/070040 | 9/2002 |
| WO | WO 2002/083046 | 10/2002 |
| WO | WO 2002/092783 | 11/2002 |
| WO | WO 2002/094256 | 11/2002 |
| WO | WO 2002/102864 | 12/2002 |
| WO | WO 2003/074100 | 9/2003 |
| WO | WO 2003/085810 | 10/2003 |
| WO | WO 2003/092620 | 11/2003 |
| WO | WO 2004/007960 | 1/2004 |
| WO | WO 2004/024300 | 3/2004 |
| WO | WO 2004/037334 | 5/2004 |
| WO | WO 2004/041064 | 5/2004 |
| WO | WO 2004/054632 | 7/2004 |
| WO | WO 2004/077387 | 9/2004 |
| WO | WO 2004/081421 | 9/2004 |
| WO | WO 2005/009488 | 2/2005 |
| WO | WO 2005/016179 | 2/2005 |
| WO | WO 2005/017000 | 2/2005 |
| WO | WO 2005/018695 | 3/2005 |
| WO | WO 2005/025447 | 3/2005 |
| WO | WO 2005/025666 | 3/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/079718 | 9/2005 |
| WO | WO 2005/082435 | 9/2005 |
| WO | WO 2005/105175 | 11/2005 |
| WO | WO 2005/105180 | 11/2005 |
| WO | WO 2005/115497 | 12/2005 |
| WO | WO 2005/118011 | 12/2005 |
| WO | WO 2005/123170 | 12/2005 |
| WO | WO 2006/014534 | 2/2006 |
| WO | WO 2006/030054 | 3/2006 |
| WO | WO 2006/034128 | 3/2006 |
| WO | WO 2006/048246 | 5/2006 |
| WO | WO 2006/052745 | 5/2006 |
| WO | WO 2006/052839 | 5/2006 |
| WO | WO-2006052338 A2 | 5/2006 |
| WO | WO 2006/056294 | 6/2006 |
| WO | WO 2006/058801 | 6/2006 |
| WO | WO 2006/062276 | 6/2006 |
| WO | WO 2006/081403 | 8/2006 |
| WO | WO 2006/092333 | 9/2006 |
| WO | WO 2006/116992 | 11/2006 |
| WO | WO 2006/117207 | 11/2006 |
| WO | WO 2006/135506 | 12/2006 |
| WO | WO 2007/002835 | 1/2007 |
| WO | WO 2007/013064 | 2/2007 |
| WO | WO 2007/019038 | 2/2007 |
| WO | WO 2007/024230 | 3/2007 |
| WO | WO 2007/030598 | 3/2007 |
| WO | WO 2007/030599 | 3/2007 |
| WO | WO 2007/030601 A2 | 3/2007 |
| WO | WO 2007/031757 | 3/2007 |
| WO | WO 2007/051599 | 5/2007 |
| WO | WO 2007/084792 | 7/2007 |
| WO | WO 2007/085396 | 8/2007 |
| WO | WO 2007/106592 | 9/2007 |
| WO | WO 2007/106594 | 9/2007 |

(56) References Cited

FOREIGN PATENT DOCUMENTS

| | | |
|---|---|---|
| WO | WO 2007/124198 | 11/2007 |
| WO | WO 2007/133618 | 11/2007 |
| WO | WO 2008/013896 | 1/2008 |
| WO | WO 2008/027449 | 3/2008 |
| WO | WO 2008/031418 | 3/2008 |
| WO | WO 2008/036345 | 3/2008 |
| WO | WO 2008/039223 | 4/2008 |
| WO | WO 2008/040020 | 4/2008 |
| WO | WO 2008/041926 | 4/2008 |
| WO | WO 2008/062176 | 5/2008 |
| WO | WO 2008/076407 | 6/2008 |
| WO | WO 2008/082444 | 7/2008 |
| WO | WO 2008/100437 | 8/2008 |
| WO | WO 2008/100440 | 8/2008 |
| WO | WO 2008/112304 | 9/2008 |
| WO | WO 2008/134544 | 11/2008 |
| WO | WO 2008/134774 | 11/2008 |
| WO | WO 2008/141228 | 11/2008 |
| WO | WO 2008/141470 | 11/2008 |
| WO | WO 2009/019227 | 2/2009 |
| WO | WO 2009/019229 | 2/2009 |
| WO | WO 2009/034322 | 3/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/066105 | 5/2009 |
| WO | WO 2009/066106 | 5/2009 |
| WO | WO 2009/070905 | 6/2009 |
| WO | WO 2009/078790 | 6/2009 |
| WO | WO 2009/089390 | 7/2009 |
| WO | WO 2009/095170 | 8/2009 |
| WO | WO 2009/098696 | 8/2009 |
| WO | WO 2009/103031 | 8/2009 |
| WO | WO 2009/111657 | 9/2009 |
| WO | WO 2009/117635 | 9/2009 |
| WO | WO 2009/120951 | 10/2009 |
| WO | WO 2009/122989 | 10/2009 |
| WO | WO 2009/124100 | 10/2009 |
| WO | WO 2009/126833 | 10/2009 |
| WO | WO 2009/145703 | 12/2009 |
| WO | WO 2009/146441 | 12/2009 |
| WO | WO 2009/151380 | 12/2009 |
| WO | WO 2009/156709 | 12/2009 |
| WO | WO 2009/158124 | 12/2009 |
| WO | WO 2009/158128 | 12/2009 |
| WO | WO 2009/158130 | 12/2009 |
| WO | WO 2010/026251 | 3/2010 |
| WO | WO 2010/033271 | 3/2010 |
| WO | WO 2010/051068 | 5/2010 |
| WO | WO 2010/051418 | 5/2010 |
| WO | WO 2010/059712 | 5/2010 |
| WO | WO 2010/072309 | 7/2010 |
| WO | WO 2010/072349 | 7/2010 |
| WO | WO 2010/072395 | 7/2010 |
| WO | WO 2010/075313 | 7/2010 |
| WO | WO 2010/083135 | 7/2010 |
| WO | WO 2010/118316 | 10/2010 |
| WO | WO 2010/120776 | 10/2010 |
| WO | WO 2010/141271 | 12/2010 |
| WO | WO 2010/142959 | 12/2010 |
| WO | WO 2010/147592 | 12/2010 |
| WO | WO 2011/019476 | 2/2011 |
| WO | WO 2011/023275 | 3/2011 |
| WO | WO 2011/082461 | 7/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2011/148188 | 12/2011 |
| WO | WO 2012/022484 | 2/2012 |
| WO | WO 2012/028842 | 3/2012 |
| WO | WO 2012/048179 | 4/2012 |
| WO | WO 2012/078707 | 6/2012 |
| WO | WO 2012/088572 | 7/2012 |
| WO | WO 2012/131237 | 10/2012 |
| WO | WO 2012/140180 | 10/2012 |
| WO | WO 2012/140378 | 10/2012 |
| WO | WO 2012/143665 | 10/2012 |
| WO | WO 2013/006932 | 1/2013 |
| WO | WO 2013/010907 | 1/2013 |
| WO | WO 2013/019017 | 2/2013 |
| WO | WO 2013/064852 | 5/2013 |
| WO | WO 2013/065423 | 5/2013 |
| WO | WO 2013/083800 | 6/2013 |
| WO | WO 2013/090810 | 6/2013 |
| WO | WO 2013/117945 | 8/2013 |
| WO | WO 2013/118447 | 8/2013 |
| WO | WO 2013/119854 | 8/2013 |
| WO | WO 2013/133652 | 9/2013 |
| WO | WO 2013/136181 | 9/2013 |
| WO | WO 2013/149078 | 10/2013 |
| WO | WO 2014/008348 | 1/2014 |
| WO | WO 2014/016759 | 1/2014 |
| WO | WO 2014/020440 | 2/2014 |
| WO | WO 2014/020443 | 2/2014 |
| WO | WO 2014/108476 | 7/2014 |
| WO | WO 2014/113253 | 7/2014 |
| WO | WO 2014/113504 | 7/2014 |
| WO | WO 2014/107285 | 9/2014 |
| WO | WO 2014/143488 | 9/2014 |
| WO | WO 2015/022334 | 2/2015 |
| WO | WO 2015/022340 | 2/2015 |
| WO | WO 2015/023515 | 2/2015 |
| WO | WO 2015/031216 | 3/2015 |

OTHER PUBLICATIONS

US 6,306,115 B1, 10/2001, Kelly et al. (withdrawn)
U.S. Appl. No. 61/828,604, filed May 29, 2013, Collinson et al.
U.S. Appl. No. 61/829,187, filed May 30, 2013, Collinson et al.
U.S. Appl. No. 61/906,865, filed Nov. 20, 2013, Collinson et al.
U.S. Appl. No. 61/907,350, filed Nov. 21, 2013, Collinson et al.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A., et al., "Treatment of the Perineal Wound after Proctectomy by Intermittent Irrigation", Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvash State University, Cheboksary, USSR 1986) pp. 94-96 (with English translation).
Braglina, I.O., et al. "Russian Chemical Bulletin", Dec. 31, 1983.
Chariker, M.E., et al., "Effective Management of Incisional and Cutaneous Fistulae with Closed Suction Wound Drainage," Contemporary Surgery. Jun. 1989, pp. 59-63, vol. 34.
Chintamani, et al., "Half versus full vacuum suction drainage after modified radical mastectomy for breast cancer—a prospective randomized clinical trial", Research Article (Jan. 27, 2005), 1-5.
Davydov, Y.A., et al., The Bacteriological & Cytological Assessment of Vacuum Therapy of Purulent Wounds, Vestnik Chirurgia 1988, October Edition 48-52 (in Russian with English translation). 1987.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in

(56) References Cited

OTHER PUBLICATIONS

Wound Care, Russian Journal: Vestnik Khirurgii, BlueSky Publishing, La Costa, California (2004), 5-7.
De Lange, M.Y., et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Hartz, R.S. et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Kalypto Medical, NPD 1000 Negative Pressure Wound Care System, Clinician & Patient Instructions for Use (publication date unknown, believed to be Feb. 2010).
Kalypto Medical, NPD 1000 Product Brochure (publication date unknown, believed to be Nov. 2010).
Kendall ULTEC Hydrocolloid Dressing (4"×4"), product ordering page, web page downloaded Jul. 13, 2014.
Khirugii, Vestnik, "A Collection of Published Studies Complementing the Research and Innovation of Wound Care", The Kremlin Papers, Perspectives in Wound Care, Russian Medical Journal, Vestnik Khirurgii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Membrane Filters, in 16 pages, from website: http://www.advantecmfs.com/catalog/filt/membrane.pdf#page=11 (date unknown, but believed to be copyright 2001-2011).
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
Nursing75, Wound Suction: Better Drainage with Fewer Problems, Nursing, vol. 5, No. 10, Oct. 1975, pp. 52-55.
Prevena™ Incision Management System, Clinician Guide, pp. 1-9, Jan. 2010.
Prevena™ Incision Management System, Patient Guide, pp. 1-2, Jan. 2010.
Protz, Kerstin: "Modern Wundauflagen unterstutzen Heilungsprozess", Wundversorgung: Indikation und Anwendung, Geriatrie Journal, Apr. 2005, pp. 3333-3339, with translation.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-534.
Svedman, P., "A Dressing Allowing Continuous Treatment of a Biosurface", IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent Irrigation," Annals of Plastic Surgery, vol. 17, No. 2, Aug. 1986, pp. 125-133.
Swift, et al., "Quorum Sensing in *Aeromonas hydrophila* and *Aeromonas salmonicida*: Identification of LuxRI Homologs AhyRI and AsaRI and Their Cognate N-Acylhomoserine Lactone Signal Molecules," J. Bacteriol., 179(17):5271-5281 (1997).
Teder et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-513, 1972 Vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 8-10.
Venturi, Mark L., "Mechanisms and Clinical Applications of the Vacuum-Assisted Closure (VAC) Device", Am J Clin Dermatol (2005) 693, 185-194; Review Article (2005), 185-194.
Vijanto, J. and J. Raekallio, Local Hyperalimentation of Open Wounds, Br. J. surg., 1976, 63, 427-430.
Webb, New Techniques in Wound Management: Vacuum-Assisted Wound Closure, Journal of the American Academy of Orthopadic Surgeons, v. 10, No. 5, pp. 303-311, Sep. 2002.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
"Technology Watch", May 1989, in 1 page.
Hersle, K et al., "Uses of Dextranomer Absorbent Pads After Cryosurgery of Cutaneous Malignancies", The Journal of Dermatologic Surgery and Oncology, vol. 8, Jan. 1982, in 4 pages.
International Search Report, re PCT Application No. PCT/GB2008/051090, dated Mar. 4, 2009.
International Preliminary Reporton Patentability, re PCT Application No. PCT/GB2008/051090, dated May 25, 2010.
Bevan, Damon, et al.: "Diverse and potent activities of HGF/SF in skin wound repair", Journal of Pathology, 2004; 203: 831-838.
English Translation of Invalidity Suit by KCI Medizinprodukte GmbH versus Kalypto Medical, Inc., concerning declaration of invalidity of the German part of the European Patent No. 2 021 046 (German application No. 60 2007 021 330.4) dated Mar. 11, 2015 in 38 pages. EP 2 021 046 is related to the present application by virtue of a common priority claim to U.S. Appl. No. 11/610,458, now U.S. Pat. No. 7,615,036, and U.S. Appl. No. 11/610,458, now U.S. Pat. No. 7,779,625.
Greer, et al., Techniques for Applying Subatmospheric Pressure Dressing to Wounds in Difficult Regions of Anatomy, JWOCN, vol. 26, No. 5, 1999 pp. 250-253.
Info V.A.C. User Manual—KCI—Dec. 2006, in 76 pages.
Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5): 925-961.
Mitchell, Richard N., et al.: "Role of Stem Cells in Tissue Homeostasis", Pocket Companion to Robbins and Cotran Pathologic Basis of Diseas, 7th Edition., 2006.
Morykwas, M. J., et al.: "Nonsurgical Modalities to Enhance Healing and Care of Soft Tissue Wounds", Journal of the Southern Orthopaedic Association, vol. 6, No. 4 Winter 1997 in 12 pages.
Smith & Nephew, "PICO Single Use Negative Pressure Wound Therapy System", spiral booklet, Mar. 2011, in 7 pages.
Preliminary Summary of Facts and Submission, re the Opposition of European Patent No. EP 3 000 448, dated Apr. 20, 2020, in 8 pages.
Consolidated List of Cited Opposition Documents, re European Patent No. EP 3 000 448, dated Jul. 22, 2019, in 1 page.
Japanese Office Action, re JP Application No. 2018-076049, dated Mar. 2, 2020.
Notice of Opposition—Statement of Facts and Evidence, re European Patent No. EP 2 214 611, dated Sep. 26, 2019, in 24 pages.
Notice of Opposition—Statement of Facts and Evidence, re European Patent No. EP 3 000 448, dated Jul. 16, 2019, in 12 pages.
Reply of the Patent Proprietor to the Notice of Opposition, re European Patent No. EP 2 214 611, dated Feb. 21, 2020, in 55 pages.
Reply of the Patent Proprietor to the Notice(s) of Opposition, re the Opposition of European Patent No. 3 000 448, dated Dec. 6, 2019, in 12 pages.
Annex to the Communication, re the Opposition of European Patent No. EP2214610, dated Mar. 3, 2020, 17 pages.

(56) References Cited

OTHER PUBLICATIONS

Davydov Y.A., et al., "Concepts of Clinico-Biological Management of Wound Process in Treatment of Purulent Wounds with the Help of Vacuum Therapy," Vestnik Chirurgia 1991, February Edition, pp. 132-135.
Notice of Opposition—Statement of Facts and Evidence of the European Patent No. 2214610, dated Jul. 8, 2019, 18 pages.
Notice of Response in Summons to Attend Oral Proceedings pursuant to rule 115(1) EPC for European Patent No. 2214611, mailed on Jun. 23, 2020, 19 pages.
Notice of Response in Summons to Attend Oral Proceedings pursuant to rule 115(1) EPC for European Patent No. 3000448, mailed on Jun. 23, 2020, 6 pages.
Reply of the Patent Proprietor to the Notice of Opposition, re the Opposition of European Patent No. 2214610, dated Dec. 3, 2019, 25 pages.
Written Submissions in Preparation to Oral Proceedings, the Opposition of European Patent No. 3000448, dated Sep. 24, 2020, 10 pages.
Kennedy J.F., et al., "Advanced Textiles for Wound Care" (Second Edition), Chapter 10, 2019, 23 pages.
BASF, Elastollan Physical Properties, 2020, 1 page.
U.S. Appl. No. 15/940,788, Wound Dressing, 2018/0214317, Mar. 29, 2018.
U.S. Appl. No. 15/962,932, Wound Dressing, 2018/0235816, Apr. 25, 2018.
U.S. Appl. No. 15/965,734, Wound Dressing, 2018/0243142, Apr. 27, 2018.
U.S. Appl. No. 16/028,258, Wound Dressing, 2018/0311078, Jul. 5, 2018.
Communication of a Notice of Opposition and Opponent's Statement of Facts and Arguments for European Patent No. 3254650, dated Sep. 30, 2020, 23 pages.
Declaration of Chris Locke submitted in the Opposition against European Patent No. EP2563308, dated Sep. 7, 2016, 6 pages.
KCI, "V.A.C. Freedom User's Guide," May 2002, 16 pages.
Opponent's Written Submission in Preparation for the Oral Proceedings, for the Opposition of European Patent No. 2214610, dated Sep. 25, 2020, 5 pages.
Proprietor's Written Submission in Preparation for the Oral Proceedings, for the Opposition of European Patent No. 2214610, dated Oct. 1, 2020, 20 pages.
Brief Communication—Letter from the Opponent, re the Opposition of European Patent No. EP2214611, dated Dec. 16, 2020, 5 pages.
Brief Communication—Letter from the Proprietor of the Patent, re the Opposition of European Patent No. EP2214611, dated Dec. 17, 2020, 54 pages.
Summons to Attend Oral Proceedings pursuant to rule 115(1) EPC and Preliminary Summary and Preliminary Opinion, re the Opposition of European Patent No. 3000448, mailed on Oct. 22, 2020, 9 pages.
Brief Communication on Oral proceedings—Letter from the Opponent, re the Opposition of European Patent No. EP2214610, dated Feb. 26, 2021, 6 pages.
Information about the result of oral proceedings for European Patent No. 2214611 mailed on Feb. 12, 2021, 23 pages.

Summons to attend oral proceedings pursuant to Rule 115(1) EPC for Patent No. EP2214610, mailed on Feb. 19, 2021, 17 pages.
Brief Communication—Letter from the Proprietor of the Patent, re the Opposition for Simmons & Simmons for European Patent No. EP3254650, dated Mar. 5, 2021, 10 pages.
3M Tegaderm, "Transparent Film Dressings," Product Profile, filed in Opposition Proceedings for European Patent No. 2214610, mailed on Aug. 4, 2020, 8 pages.
Brief Communication—Letter from the Opponent, re the Opposition of European Patent No. 3000448, dated Apr. 21, 2021, 3 pages.
Brief Communication—Letter from the Proprietor of the Patent, re the Opposition for Simmons & Simmons for European Patent No. 3000448, dated Apr. 23, 2021, 12 pages.
Information about the result of oral proceedings for European Patent No. 3000448, mailed on Jun. 14, 2021, 7 pages.
Interlocutory decision in Opposition proceedings (Art. 101 (3)(a) and 106(2) EPC) for European patent No. 2214611, mailed on May 20, 2021, 87 pages.
Minutes of the Oral Proceedings, Opposition Procedure and Summary of Facts and Submissions of European Patent No. 3000448, mailed on Jul. 22, 2021, 46 pages.
Summons to Attend Oral Proceedings Pursuant to Rule 115(1) EPC for European Patent No. 3254650, dated Jul. 19, 2021, 13 pages.
Written Submission by the Opponent re the Opposition Proceedings for European Patent No. 2214610, mailed on Aug. 4, 2021, 2 pages.
Written Submission by the Proprietor re the Opposition Proceedings for European Patent No. 2214610, mailed on Aug. 6, 2021, 23 pages.
Brief Communication—Letter from the Proprietor of the Patent, re the Opposition for Simmons & Simmons for European Patent No. 3360519, dated Jan. 3, 2022, 15 pages.
Decision revoking the European Patent (Art. 101 (3)(b) EPC) for European Patent No. 2214610, mailed on Nov. 15, 2021, 43 pages.
Decision to Maintain the Patent in Amended form for European Patent No. 3000448, dated Feb. 10, 2022, 1 page.
Forwarding of submissions to parties of a letter of the Opponent for European Patent No. 2214611, dated Feb. 7, 2022, 9 pages.
Information about the Result of Oral Proceedings, the Opposition of European Patent No. 2214610, dated Oct. 8, 2021, 7 pages.
Maintenance of the Patent with the Documents specified in the Final Decision, the Opposition of European Patent No. 3000448, mailed on Nov. 3, 2021, 1 page.
Notice of Opposition—Opponents' Statement of Facts and Arguments of the European Patent No. 3360519, dated Aug. 12, 2021, 12 pages.
Reply to Appeal—Letter of the patent proprietor for the European Patent No. 2214611, mailed on Jan. 24, 2022, 17 pages.
Statement of Ground of Appeal filed by Opponent for European Patent No. 2214611 mailed on Sep. 20, 2021, 3 pages.
Statement of Grounds of Appeal filed by proprietor for European patent No. 2214611, mailed on Sep. 30, 2021, 46 pages.
Termination of Opposition Proceedings for European Patent No. 3000448, dated Feb. 4, 2022, 1 page.
Thomas, Dr. S., "SMTL Dressings Datacard—Opsite IV 3000", Surgical Materials Testing Lab, webpage last modified Mar. 2002, 2 pages. URL: http://www.dressings.org/Dressings/opsite-iv3000.html.
U.S. Appl. No. 15/457,709, Wound Dressing, filed Mar. 13, 2017.
U.S. Appl. No. 15/610,031, Wound Dressing, filed May 31, 2017.

\* cited by examiner

WOUND DRESSING

This application is a continuation of U.S. application Ser. No. 14/869,826, filed Sep. 29, 2015, which is a continuation of U.S. application Ser. No. 14/259,026, filed Apr. 22, 2014, which is a continuation of U.S. application Ser. No. 12/744,277, filed Sep. 20, 2010, now U.S. Pat. No. 8,764,732, which is the U.S. National Phase of PCT International Application No. PCT/GB2008/051090 filed on Nov. 20, 2008, designating the United States and published on May 28, 2009 as WO 2009/066106, which claims priority to Great Britain Patent Application No. 0722820.8, filed Nov. 21, 2007, and Great Britain Patent Application No. 0817020.1, filed Sep. 17, 2008. The disclosure of these prior applications are incorporated by reference in their entireties and should be considered a part of this specification.

The present invention relates to a method and apparatus for dressing a wound and a method for manufacturing a wound dressing. In particular, but not exclusively, the present invention relates to a wound dressing useable during topical negative pressure (TNP) therapy in which the wound dressing itself acts as a waste canister to collect and store wound exudate removed from a wound site.

There is much prior art available relating to the provision of apparatus arid methods of use thereof for the application of topical negative pressure (TNP) therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, apparatus, a wound dressing and a method for cleansing a wound using aspiration, irrigation and cleansing wounds are described. Again, in very general terms, the invention described in this document utilizes similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above-noted references is included herein by reference.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

During TNP therapy a portable or non-portable therapy unit generates a negative pressure at a wound site. As fluid, including air as well as wound exudate material is removed from the wound site this must be collected in some manner remote from the wound site. With prior known therapy units 'the collection and storage of wound exudate material is typically carried out by a waste canister connected to a pump unit of the therapy unit. The use of a canister, however, can result in the therapy unit apparatus itself being quite bulky and expensive to manufacture. Also replacing a canister or a bag in a canister in which wound exudate is collected can be a time consuming and relatively unhygienic process.

Prior known therapy units also tend to include a pump which is used to generate the negative pressure. Such pumps can be costly to manufacture and are relatively heavy.

WO 2007/030601, which is incorporated herein by reference discloses a self-contained wound dressing with a micro pump. The pump for drawing wound fluid into a vacuum zone is included in a wound dressing itself. Nevertheless wound exudate from the dressing can only be removed via a complex series of steps. The exudate removal process is also prone to contamination since once an absorbent layer is fully saturated with wound exudate an access door must be opened in the wound dressing so that the absorbent layer and micro pump can be removed. It will be appreciated that such exudate removal and pump removal can be time consuming and can lead to cross contamination between users. A further problem is that the wound dressing is prone to over expansion and rupture.

It is an aim of the present invention to at least partly mitigate the above-mentioned problems.

It is an aim of certain embodiments of the present invention to provide a method for providing negative pressure at a wound site to aid in wound closure and healing in which wound exudate drawn from a wound site during the therapy is collected and stored in a wound dressing.

It is an aim of certain embodiments of the present invention to provide a wound dressing which is able to be placed over a wound site and which includes an integrated pump to generate negative pressure at that wound site. Also for certain embodiments the wound dressing can collect any wound exudate.

According to a first aspect of the present invention there is provided apparatus for dressing a wound, comprising:
an absorbent layer for absorbing wound exudate;
a liquid impermeable, gas permeable filter layer over the absorbent layer; and a cover layer comprising at least one orifice;
wherein the absorbent layer is in fluid communication with the filter layer.

According to a second aspect of the present invention there is provided a method of applying topical negative pressure (TNP) at a wound site, comprising the steps of:
pumping wound exudate and air from a wound site, a peripheral region around the wound site being sealed with a wound dressing;
collecting wound exudate, pumped from the wound site in an absorbent layer of the wound dressing; and
exhausting gas through at least one orifice in a cover layer of the wound dressing
and a filter layer in fluid communication with the absorbent layer.

Certain embodiments of the present invention provide the advantage that a disposable wound dressing can be fixed over a wound site and can simultaneously be used to provide negative pressure at the wound site and collect and store wound exudate.

Certain embodiments of the present invention provide the advantage that a separate therapy unit is not required to generate negative pressure at a wound site and collect and store any wound exudate. Rather a wound dressing can carry out both a pumping and wound exudate collecting process. The wound dressing may then be a one use item which can be disposed of subsequent to use. This reduces a risk of contamination.

Certain embodiments of the present invention provide the advantage that a wound dressing can be used to collect wound exudate generated during a negative pressure therapy process. A pump remote from the wound dressing can be connected to the wound dressing and reused whilst the wound dressing itself is used to collect wound exudate and may then be disposed of after use.

Figure 3:
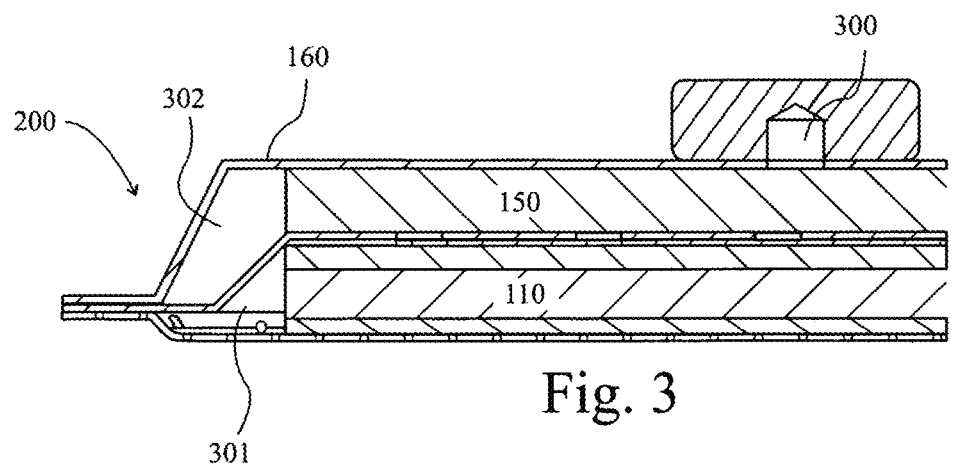
Figure 2:
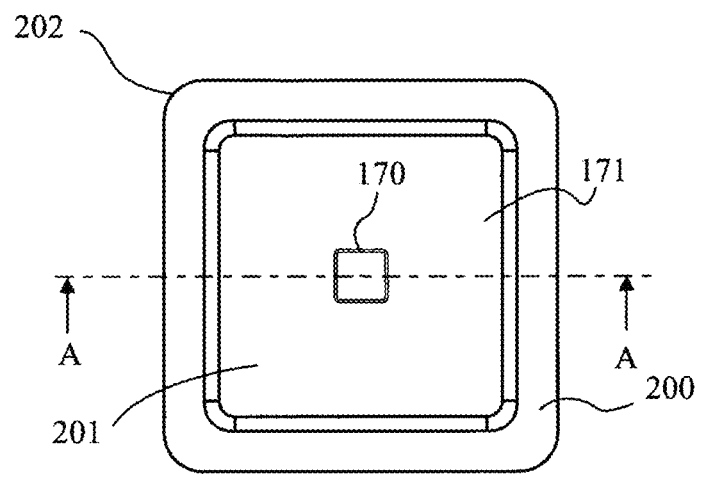
Figure 5:
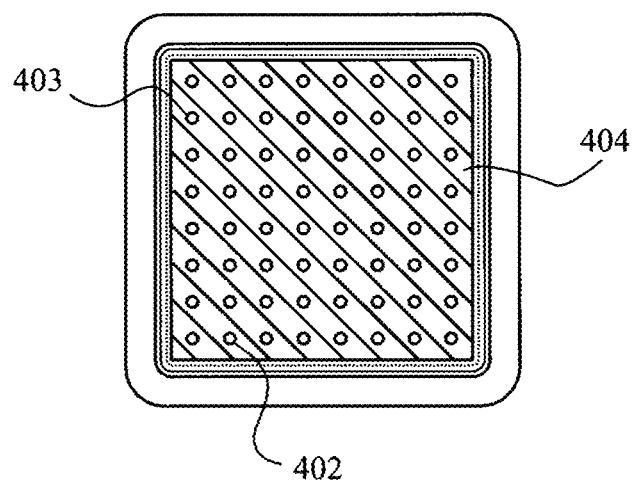
Figure 4:
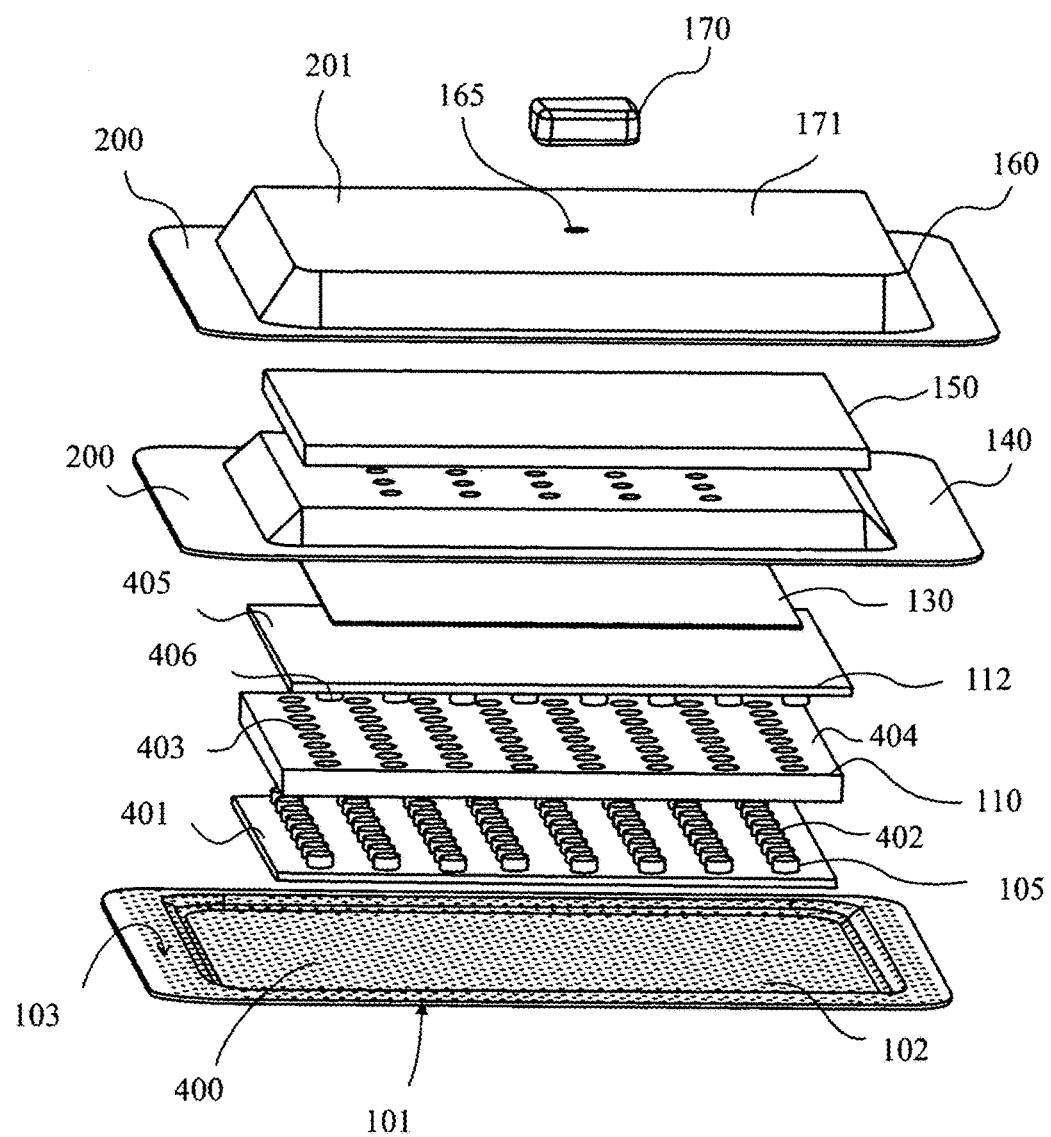

Embodiments of the present invention will now be described hereinafter, by way of example only, with reference to the accompanying drawings in which:

FIG. 1 illustrates a wound dressing;
FIG. 2 illustrates a top view of a wound dressing;
FIG. 3 illustrates a portion of the wound dressing;
FIG. 4 illustrates an exploded view of a wound dressing with a mounted pump; and
FIG. 5 illustrates a view of a horizontal section through a wound dressing.

In the drawings like reference numerals refer to like parts.

FIG. 1 illustrates a cross section through a wound dressing 100 according to an embodiment of the present invention. A plan view from above of the wound dressing 100 is illustrated in FIG. 2 with the line A-A indicating the location of the cross section shown in FIG. 1. It will be understood that FIG. 1 illustrates a generalised schematic view of an apparatus 100. It will be understood that embodiments of the present invention are generally applicable to use in topical negative pressure (TNP) systems. Briefly, negative pressure wound therapy assists in the closure and healing of many forms of "hard to heal" wounds by reducing tissue oedema; encouraging blood flow and granular tissue formation; removing excess exudate and reducing bacterial load (and thus infection risk). In addition, the therapy allows for less disturbance of a wound leading to more rapid healing.

The wound dressing 100 can be located over a wound site to be treated. The dressing 100 forms a sealed cavity over the wound site. Optionally wound packer can be used within a wound cavity below the dressing. Aptly the packer material can be a gauze or reticulated PU foam material.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

As illustrated in FIG. 1 a lower surface 101 of the wound dressing 100 is provided by an optional wound contact layer 102. The wound contact layer 102 can be a polyurethane layer or polyethylene layer or other flexible layer which is perforated, for example via a hot pin process or in some other way, or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations are small enough to meet this requirement but still allow fluid through. The wound contact layer also helps hold the whole wound dressing together and acts as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive which may be a silicone or acrylic based adhesive or other such adhesives may be formed on both sides or optionally on a selected one or none of the sides of the wound contact layer. When a lower pressure sensitive adhesive layer is utilised this helps adhere the wound dressing to the skin around a wound site.

An optional layer 105 of porous material such as a foam layer or the like is located above the wound contact layer. This porous layer allows transmission of fluid including liquid and gas away from a wound site into upper layers of the wound dressing. The layer 105 also helps distribute pressure generated by a pump, mentioned in more detail below, so that a whole wound site sees an equalised negative pressure. Reticulated foam or a non-woven material which might be natural or synthetic can be used as the porous material of the porous layer 105.

A layer 110 of absorbent material is provided above the transmission layer 105 or where no lower transmission layer is used on the wound contact layer or where no transmission layer 105 or wound contact layer 102 are used the absorbent layer lower surface forms the wound contact layer. The absorbent material which may be a foam or non-woven natural or synthetic material and which may optionally include or be super-absorbent material forms a reservoir for fluid, particularly liquid, removed from the wound site. The material of the absorbent layer also prevents liquid collected in the wound dressing from flowing in a sloshing manner. The absorbent layer 130 also helps distribute fluid throughout the layer via a wicking action so that fluid is drawn from the wound site and stored throughout the absorbent layer. This prevents agglomeration in areas of the absorbent layer. Since in use the absorbent layer experiences negative pressures the material of the absorbent layer is chosen to absorb liquid under such circumstances. Superabsorber material is an example of such a material. Non superabsorber material can be utilised however even where significant negative pressures are envisaged. The material of the absorbent layer does not need to be hydrophilic. Aptly a material with connective open voids can be used. Aptly a material is used that can resist the compressive force of the negative pressure e.g. precompressed FT11M foam manufactured by Foam Techniques. Aptly the absorbent material is selected so that fluid is prevented from draining back out when the dressing is removed. It is to be noted that if a superabsorber is used such a material is able to expand against the compressive force of the negative pressure.

A further optional layer 112 of porous material such as a foam layer or the like is located above the absorbent layer 110. This porous layer allows transmission of fluid including liquid and gas away from a wound site into upper layers of the wound dressing. The layer 112 also helps distribute pressure generated by a pump, mentioned in more detail below, so that a whole wound site sees an equalised negative pressure. Reticulated foam or a non-woven material which might be natural or synthetic can be used as a porous material of the porous layer 112. The material may the same or different from the previously mentioned layer 105 of porous material.

A filter layer 130 is provided over the absorbent layer 110. The filter layer permits moisture vapour and gas but no liquid through. A suitable material for the filter material of the filter layer 130 is 0.2 micron Gore™ expanded PTFE from the MMT range. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter.

It will be understood that other types of material could be used for the filter layer. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. Aptly the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleo phobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter layer 130 thus enables gas to be exhausted upwards through the wound dressing. Liquid, particulates and pathogens however are contained in the dressing.

A gas impermeable sealing layer 140 extends across the width of the wound dressing. The sealing layer which may, for example, be a polyurethane film having a pressure sensitive adhesive on both sides is impermeable to gas and this layer thus operates to seal a wound cavity over which the wound dressing is placed. In this way an effective chamber is made beneath the sealing layer and between the sealing layer and a wound site where a negative pressure can be established. The sealing layer 140 is sealed to the filter layer 130. For example via adhesive or welding techniques. Gas leaving the dressing thus passes through the filter layer and sealing layer.

Aptly the material of the sealing layer can have a high moisture vapour permeability for example Elastollan (Trade name) SP9109 manufactured by BASF. A dotted pattern spread acrylic adhesive can optionally be used to help improve moisture vapour permeability. An advantage of using a high moisture vapour permeability material as the sealing layer 160 is that the fluid handling capacity of the dressing may be increased significantly by the action of moisture transpiring through the film and dispersing into the atmosphere. Advantageously, transpiration rates can be easily achieved of the order of 3000 grams/meter square/24 hours as a result of the high humidity achieved in the dressing and intimate contact of material achieved during use of the apparatus at a negative pressure of up to 250 mmHg below atmospheric pressure.

As illustrated in FIG. 1 a grid array of through holes 141 are provided in the sealing layer. These enable fluid including gas and liquid to pass through the sealing layer 140. Alternatively where a separate cover layer and sealing layer are used the sealing layer may extend around only a circumferential area of the underlying layers where it seals between an outer layer (mentioned below in more detail) and the filter layer. As a result any gas leaving the wound site must leave via the filter layer. Liquid is retained in layers below the filter layer.

A layer 150 of porous material such as a foam layer or the like is located above the sealing layer 140. This porous layer allows transmission of fluid including liquid and gas away from a wound site. The layer 150 also helps distribute pressure generated by a pump, mentioned in more detail below, so that a whole wound site sees an equalised negative pressure. Reticulated foam or a non-woven material which might be natural or synthetic can be used as the porous material of the layer 150. The material may be the same or different from the material of the underlying layers 105, 112.

A cover layer 160 covers the absorbent layer of the wound dressing 100. The cover layer which, for example, may be a polyurethane film acts as a bacterial barrier and helps hold in liquid to stop fouling. The cover layer also provides integrity for the dressing and is impermeable to moisture vapour and gas. The cover layer helps hold the wound dressing together thus providing structural integrity. An upper surface 171 also presents a bacteria free non soiling surface. As an alternative the material of the cover layer can have a high moisture vapour permeability, for example Elastollan (Trade name) SP9109 manufactured by BASF. A dotted pattern spread acrylic adhesive can optionally be used to help improve moisture vapour permeability. An advantage of using a high moisture vapour permeability material as the cover layer 160 is that the fluid handling capacity of the dressing may be increased significantly by the action of moisture transpiring through the film and dispersing into the atmosphere. Advantageously, transpiration rates can be easily achieved of the order of 3000 grams/meter square/24 hours as a result of the high humidity achieved in the dressing and intimate contact of material achieved during use of the apparatus at a negative pressure of up to 250 mmHg below atmospheric pressure.

A single aperture 165 farmed as a single hole or close arrangement of holes is formed in a central region of the upper cover layer. The aperture 165 is in fluid communication with an inlet to a pump 170 which is mounted on the upper surface 171 of the cover layer. In operation the pump 170 pumps fluid through the wound dressing from a wound site below the wound contact layer 102 upwards through the first transmission layer 105, absorbent layer 110, further transmission layer 112, filter layer 130, sealing layer 140, and further transmission layer 150.

Turning to FIG. 2 which illustrates a wound dressing 100 in accordance with an embodiment of the present invention one can see the upper surface 171 of the cover layer 170 which extends radially outwardly away from a centre of the dressing into a border region 200 surrounding a central raised region 201 overlying the foam layers and layer 110 of absorber. FIG. 2 also helps illustrate the location of the pump 170 on the cover layer. As indicated in FIG. 2 the general shape of the wound dressing is a square having equal side lengths with rounded corner regions 202. It will be appreciated that wound dressings according to other embodiments of the present invention can be shaped differently such as rectangular, circular or elliptical dressings.

FIG. 3 illustrates an expanded view of the border region 200 of the wound dressing 100 illustrated in FIGS. 1, 2 and 3. As seen, the cover layer 160 extends over the foam transmission layer 150 into an edge region. Here the cover layer is secured to the sealing layer 140 and the wound contact layer 102. FIG. 3 also helps illustrate how the perforations 104 in the wound contact layer 102 extend around the foam layer 105 and absorbent layer 110. It will be noted that a space 301 is indicated in FIG. 3 underneath the sealing layer 140 and above the wound contact layer 102 and ends of the transmission layers 105, 112 and absorbent layer 110. The space 301 is shown for illustrative reasons only and in practice the transmission layers and absorbent layers will be bevelled somewhat so as to reduce the space. A further space 302 is likewise illustrated in FIG. 3 above the sealing layer and below the inner surface of the cover layer. Again this is included for illustration only and in practice these spaces will be avoided due to a nipping process in the method of manufacture. It will also be appreciated by those skilled in the art that when put in use the wound dressing will be subject to a negative pressure within a region defined by the inner surface of the cover layer. Such a negative pressure will tend to collapse any remaining spaces.

It will be understood that according to embodiments of the present invention the wound contact layer is optional. This layer is, if used, porous to water and faces an underlying wound site. A lower porous layer 105 such as a reticulated PU foam layer is used to distribute gas and fluid removal such that all areas of a wound are subjected to equal pressure. The sealing layer together with the filter layer forms a substantially liquid tight seal over the wound. Thus as the pump 170 pumps a negative pressure is generated below the sealing layer. This negative pressure is thus experienced at the target wound site. Fluid including air and wound exudate is drawn through the wound contact layer and reticulated foam layer 105. The wound exudate drawn through the lower layers of the wound dressing is dissipated and absorbed into the absorbent layer where it is collected and stored. Air and moisture vapour is drawn upwards through the wound dressing through the intermediate transmission layer 112 and through the filter layer and sealing layer. The filter layer and sealing layer are secured together so as to prevent upward movement through the wound dressing of anything other than moisture vapour and air. This air and moisture vapour is drawn upwards by the pump 170 into the fluid inlet 300. The pump exhausts the fluid as air and moisture vapour through a fluid exit (not shown).

It is to be noted that the upper transmission layer 150 and cover layer 160 are optional. Their use is helpful during multi orientation use when portions of the filter layer might otherwise become occluded. When a separate cover layer 160 is not utilised the sealing layer also performs the extra function of covering the dressing and will thus additionally act as a cover layer.

It will be appreciated by those skilled in the art that rather than have a cover layer overlying the filter layer the cover layer may itself be overlain by a filter layer. The cover layer may thus be the outermost layer of the wound dressing or the filter layer may be the outermost layer of the wound dressing. Further outer layers (not shown) may optionally be used so long as they are gas and water vapour permeable.

As still further options the dressing can contain antimicrobial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilised. As a still further option odour trapping elements such as activated carbon, cyclodextrine, zealite or the like may be included in the absorbent layer or as a still further layer above the filter layer.

FIG. 4 illustrates an exploded view of the wound dressing illustrated in FIGS. 1, 2 and 3. As illustrated in FIG. 4 the lower-most layer of the wound dressing is a perforated wound contact layer 102. It will be appreciated that prior to use a still lower protective layer may be secured to the lower surface 101 of the wound contact layer. The protective paper (not shown) is removed immediately prior to application of the wound dressing over a wound site. During manufacture a central region 400 of the wound contact layer 102 is made slightly concave so as to provide a dished upper surface 103 for the wound contact layer.

A transmission layer 105 is duly located in the dished central region 400 of the wound contact layer. The foam layer includes a substantially rectangular base region 401 together with an array of upstanding columns 402. As illustrated in FIG. 4 an array of 8×8 columns 402 may be used. It will be appreciated that other numbers of columns may be utilised. The columns 402 have a substantially circular cross section although it will be appreciated that column elements having different cross section shapes could be used. The column elements 402 and base section 402 are aptly integrally formed although these could be separately formed with the column elements being secured to the base section in some appropriate way such as via adhesive techniques.

The absorbent layer 110 is located above the transmission layer 105. The absorbent layer 110 is a layer of absorbent material and includes through holes 403 formed in a substantially rectangular block 404 of absorbent material. The through holes are set out in an 8×8 array to coincide with the upstanding columns 402 in the underlying transmission layer. It will be appreciated that the number and pattern of through bores 403 is selected to tally with the shape and number and arrangement of the columns.

The intermediate transmission layer 112 is a substantially rectangular base section 405 of porous material such as reticulated foam with an array of columns 406 extending downwardly from a lower surface of the base 405. The columns 406 coincide with locations of the through bores 403 in the absorbent layer. It will be appreciated that the columns 406 of the intermediate transmission layer 112 may be integrally formed with the base portion 405 of the transmission layer or may be secured in some fashion thereto. The height of the columns 402,406 of the lower and intermediate transmission layers respectively is such that an upper contact surface of the columns 402 of the lower transmission layer and a lower contact surface of the columns 406 of the intermediate transmission layer contact when the wound dressing is put together. These thus provide fluid transmission paths through the absorber layer so that fluid, including air and wound exudate and liquid, is drawn from the lower region upwardly through the absorbent layer when the pump 170 is operating.

A rectangular layer of filter material 130 is located above the upper surface of the base section 405 of the intermediate transmission layer. The filter layer blocks movement therethrough of liquid. The filter layer is aptly a 0.2 micron Gore™ expanded PTFE sheet.

A sealing layer 140 is located over the filter layer 130. The sealing layer has a border region and a generally concave central region 407. The underside of the sealing layer 140 is thus recessed. An array of apertures set out in a 5×5 grid array is made through the sealing layer 140. The sealing layer away from the apertures is gas and fluid tight. If a material having a high moisture vapour permeability is optionally used then the sealing layer will of course be permeable to moisture vapour. Fluid, including liquid and gas, can of course penetrate through the perforations. The filter layer 130 which is secured on the underside of the sealing layer, however, prevents liquid penetration through the apertures and to an extent prevents penetration of air through the apertures. Moisture vapour can penetrate through the apertures.

An upper transmission layer formed as a sheet of reticulated foam is located over the central region of the upper surface of the sealing layer 140. The upper transmission layer acts as a manifold and diffuser to help spread the negative pressure generated by the pump 170.

A cover layer 160 is located over the sealing layer and upper transmission layer 150. The cover layer has a border region 200 and a central raised region 201. The underside of the cover layer thus presents a central dished region to receive the upper transmission layer, raised central region of the sealing layer and the filter layer, intermediate transmission layer, absorbent layer and lower transmission layer. A central aperture 165 is made in the centre of the upper surface of the cover layer. The central aperture 165 is located to coincide with a fluid inlet 300 of the pump 170. Thus in use when a pump 170 is in use a negative pressure is generated under the cover 160. This negative pressure is distributed throughout the wound dressing and at a target wound site located under the wound contact layer. As the negative pressure is established and maintained wound exudate and air is drawn upwards away from the wound site through the wound dressing. Liquid and air is drawn upwards through the wound contact layer into the base of the lower transmission layer 105 and upwards through the connecting columns in the lower transmission layer and intermediate transmission layer. It will be appreciated of course that columns having a height sufficient to bridge the whole of the absorbent layer could be provided on either the upper surface of the lower transmission layer 105 or the lower surface of the intermediate transmission layer 112. Alternatively the apertures 403 in the absorbent layer may be filled with transmissive material such as foam cylinders when the wound dressing is manufactured. Any wound exudate being drawn upward through the wound dressing is dissipated outwardly from the absorbent material in the aperture regions of the absorbent layer. The liquid is thus collected and stored in the absorbent layer. Air and moisture vapour carries on upwards through the filter layer 130 and sealing layer 140 and is evacuated by the pump 170.

FIG. 5 illustrates a horizontal cross section through the wound dressing illustrating an upper surface 404 of the absorbent layer including apertures 403. Each of the apertures 403 is filled with absorbent material such as columns 402 from the lower intermediate layer.

It will be appreciated that according to certain embodiments of the present invention fluid communication paths through which fluid can be transmitted from the lower transmission layer to the intermediate transmission layer can be made by pinching together peripheral regions of the lower and intermediate regions. Fluid transmission would thus proceed around the peripheral edges of the wound dressing. Such fluid paths may replace the fluid paths formed by the columns passing through apertures in the absorbent layer or may alternatively take the place of such passageways. This would maximise the quantity of absorber material in the layer 110 in the resultant wound dressing.

It is to be noted that according to certain other embodiments of the present invention a remote pump may be mounted to a border region of the wound dressing rather than onto the top surface. In such case tubes may be connected directly to the pump. Subsequent to a single use the wound dressing and pump may thus be discarded. As an option the tubes may be provided with a click fit connector or other easy fit connector which can be connected to corresponding mating connectors joined via corresponding tubes to a remote pump. In this way a remote pump may be reused whilst the wound dressing itself including connecting tubes and connectors is disposable after a single use.

It will be appreciated that alternatively the tubes could be provided by a single dual lumen tube. As a still further alternative the tubes may be provided by a single continuous looped tube, the tube then passing through pinch rollers for a peristaltic pump.

It will be understood that for embodiments of the present invention which include a pump mounted on the cover layer or on a peripheral border area of the dressing an integral power source and control circuitry can be included. Alternatively the power source can be external to the pump and remotely mounted. A remote power source and/or control circuitry improves the disposability of the dressing and permits battery recharge if spare batteries are used.

It is to be noted that in use the dressing may be used "up-side down", at an angle or vertical. References to upper and lower are thus used for explanation purposes only.

Where a separate cover layer and sealing layer are utilised such layers may be manufactured from the same or different materials.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method for treating a tissue site with reduced pressure, the method comprising:
   positioning a porous member proximate to the tissue site;
   covering the porous member with a sealing layer having at least one aperture to form a sealed space over the porous member and the sealing layer comprising a dotted pattern spread adhesive;
   maintaining reduced pressure under the sealing layer within the sealed space; and
   transpiring moisture from the sealed space through the sealing layer into the atmosphere while reduced pressure is maintained under the sealing layer within the sealed space, wherein the sealing layer transpires moisture at a rate of at least about 3000 grams/meter square/24 hours;
   wherein the dotted pattern spread adhesive is spread across the sealing layer in a manner to improve moisture vapor permeability and the transpiration of moisture to the atmosphere compared to a sealing layer fully covered with adhesive.

2. The method of claim 1, wherein moisture vapour penetrates through the at least one aperture.

3. The method of claim 1, wherein the at least one aperture in the sealing layer is covered by a liquid impermeable membrane.

4. The method of claim 1, wherein the sealing layer is made of a moisture vapour permeability material.

5. The method of claim 1, further comprising maintaining a pressure differential across the sealing layer when reduced pressure is maintained within the sealed space.

6. The method of claim 1, further comprising positioning a non-woven absorbent material in the sealed space.

7. The method of claim 1, wherein the adhesive comprises a pressure-sensitive adhesive.

8. A method of manufacturing a dressing for treating a tissue site, the method comprising:
   providing a porous member for placing proximate to the tissue site;
   providing a sealing layer having at least one aperture and comprising a dotted pattern spread adhesive, wherein the sealing layer is configured to transpire moisture at a rate of at least about 3000 grams/meter square/24 hours while maintaining a reduced pressure under the sealing layer; and
   securing a membrane relative to the sealing layer to cover the at least one aperture, wherein the membrane is configured to permit penetration of moisture vapour through the sealing layer;
   wherein the dotted pattern spread adhesive is spread across the sealing layer in a manner to improve moisture vapor permeability and the transpiration of moisture to the atmosphere compared to a sealing layer fully covered with adhesive.

9. The method of claim 8, wherein the moisture vapour penetrates through the at least one aperture in the sealing layer.

10. The method of claim 8, wherein the sealing layer is made of a moisture vapour permeability material configured to transpire moisture from within the dressing into the atmosphere.

11. The method of claim 8, further comprising providing a non-woven absorbent material between the porous member and the sealing layer.

12. The method of claim 8, wherein the adhesive comprises a pressure-sensitive adhesive.

13. A dressing for treating a tissue site with reduced pressure, the dressing comprising:
   a porous member configured to be positioned proximate to the tissue site; and
   a sealing layer configured to form a sealed space over the porous member and maintain reduced pressure under the sealing layer within the sealed space, the sealing layer having at least one aperture and being configured to transpire moisture from the sealed space through the sealing layer into the atmosphere, wherein the sealing layer is configured to transpire moisture at a rate of at least about 3000 grams/meter square/24 hours; and
   wherein the sealing layer comprises a dotted pattern spread adhesive and wherein the dotted pattern spread adhesive is spread across the sealing layer in a manner to improve moisture vapor permeability and the transpiration of moisture to the atmosphere compared to a sealing layer fully covered with adhesive.

14. The dressing of claim 13, wherein the sealing layer is configured to maintain a pressure differential across the sealing layer when reduced pressure is maintained within the sealed space.

15. The dressing of claim 13, wherein the dressing further comprises a non-woven absorbent material.

16. The dressing of claim 13, wherein the adhesive comprises a pressure-sensitive adhesive.

* * * * *